(12) United States Patent
Makower et al.

(10) Patent No.: US 8,556,925 B2
(45) Date of Patent: Oct. 15, 2013

(54) DEVICES AND METHODS FOR TREATMENT OF OBESITY

(75) Inventors: Joshua Makower, Los Altos, CA (US); Theodore M. Bender, Oakland, CA (US); Brian K. Shiu, Sunnyvale, CA (US); Pablo G. Acosta, Newark, CA (US); Shuji Uemura, San Francisco, CA (US); Josef L. Friedmann, Boulder Creek, CA (US); Crystine Lee, Vallejo, CA (US)

(73) Assignee: Vibrynt, Inc., Mountain View, CA (US)

( * ) Notice: Subject to any disclaimer, the term of this patent is extended or adjusted under 35 U.S.C. 154(b) by 991 days.

(21) Appl. No.: 11/974,444

(22) Filed: Oct. 11, 2007

(65) Prior Publication Data

US 2009/0099588 A1    Apr. 16, 2009

(51) Int. Cl.
*A61M 29/00* (2006.01)

(52) U.S. Cl.
USPC .......................................... 606/192; 606/191

(58) Field of Classification Search
USPC .................................. 606/191, 192
See application file for complete search history.

(56) References Cited

U.S. PATENT DOCUMENTS

| | | | |
|---|---|---|---|
| 233,475 | A | 10/1880 | Cook et al. |
| 659,422 | A | 10/1900 | Shidler |
| 789,467 | A | 1/1905 | Wanamaker et al. |
| 769,467 | A | 5/1905 | West |
| 1,461,524 | A | 7/1923 | Goddard |
| 2,579,192 | A | 12/1951 | Kohl et al. |
| 2,646,298 | A | 7/1953 | Leary |
| 2,697,624 | A | 12/1954 | Thomas et al. |
| 2,734,299 | A | 2/1956 | Masson |
| 2,825,592 | A | 3/1958 | Semple |
| 3,326,586 | A | 6/1967 | Frost et al. |
| 3,373,140 | A | 3/1968 | Bloch |
| 3,470,834 | A | 10/1969 | Bone |

(Continued)

FOREIGN PATENT DOCUMENTS

| | | |
|---|---|---|
| EP | 1 016 377 A2 | 7/2000 |
| EP | 1520563 | 4/2005 |

(Continued)

OTHER PUBLICATIONS

McMillan, et al., Arthroscopic Knot-tying techniques, pp. 81-95, 2003.

(Continued)

*Primary Examiner* — Gary Jackson
*Assistant Examiner* — Diane Yabut
(74) *Attorney, Agent, or Firm* — Law Office of Alan W. Cannon

(57) ABSTRACT

Implantable devices, methods of implantation and tools for performing the implantations. A device includes a volume occupying member having a working configuration such that, when the device is implanted into the abdominal cavity of the patient, the device performs at least one of: prevention of expansion of the stomach of the patient into a space occupied by the volume occupying member in the abdominal cavity; and compression of a portion of the stomach. A device is configured to have substantially neutral buoyancy or a slightly positive buoyancy when implanted in the abdominal cavity external of the stomach. An attachment member is connected to the volume occupying member, and at least a portion of the attachment member is configured to encourage tissue ingrowth from at least one internal abdominal structure when held in contact therewith.

3 Claims, 25 Drawing Sheets

(56) References Cited

U.S. PATENT DOCUMENTS

| | | |
|---|---|---|
| 3,521,918 A | 7/1970 | Hammond |
| 3,571,864 A | 3/1971 | Emile et al. |
| 3,664,435 A | 5/1972 | Klessig |
| 3,675,639 A | 7/1972 | Cimber |
| 3,713,680 A | 1/1973 | Pagano |
| 3,756,638 A | 9/1973 | Stockberger |
| 3,931,667 A | 1/1976 | Merser et al. |
| 3,976,079 A | 8/1976 | Samuels et al. |
| 4,006,747 A | 2/1977 | Kronenthal et al. |
| 4,060,089 A | 11/1977 | Noiles |
| 4,133,315 A | 1/1979 | Berman et al. |
| 4,210,148 A | 7/1980 | Stivala |
| 4,246,893 A * | 1/1981 | Berson .................... 128/898 |
| 4,291,698 A | 9/1981 | Fuchs et al. |
| 4,328,805 A | 5/1982 | Akopov et al. |
| 4,416,267 A | 11/1983 | Garren et al. |
| 4,458,681 A | 7/1984 | Hophins |
| 4,472,226 A | 9/1984 | Redinger et al. |
| 4,485,805 A | 12/1984 | Foster, Jr. et al. |
| 4,493,323 A | 1/1985 | Albright et al. |
| 4,558,699 A | 12/1985 | Bashour |
| 4,592,339 A | 6/1986 | Kuzmak et al. |
| 4,592,342 A | 6/1986 | Salmasian |
| 4,621,640 A | 11/1986 | Mulhollan et al. |
| 4,669,473 A | 6/1987 | Richards et al. |
| 4,694,827 A | 9/1987 | Weiner et al. |
| 4,696,288 A | 9/1987 | Kuzmak et al. |
| 4,705,040 A | 11/1987 | Mueller et al. |
| 4,714,281 A | 12/1987 | Peck |
| 4,723,547 A | 2/1988 | Kullas et al. |
| 4,738,255 A | 4/1988 | Goble et al. |
| 4,739,758 A | 4/1988 | Lai et al. |
| 4,744,364 A | 5/1988 | Kensey |
| 4,750,492 A | 6/1988 | Jacobs |
| 4,803,985 A | 2/1989 | Hill |
| 4,823,794 A | 4/1989 | Pierce |
| 4,899,747 A | 2/1990 | Garren et al. |
| 4,955,913 A | 9/1990 | Robinson |
| 5,002,550 A | 3/1991 | Li |
| 5,033,481 A | 7/1991 | Heyler, III |
| 5,041,129 A | 8/1991 | Hayhurst et al. |
| 5,084,061 A | 1/1992 | Gau et al. |
| 5,100,421 A | 3/1992 | Christoudias |
| 5,112,310 A | 5/1992 | Grobe |
| 5,123,914 A | 6/1992 | Cope |
| 5,129,912 A | 7/1992 | Noda et al. |
| RE34,021 E | 8/1992 | Mueller et al. |
| 5,151,086 A | 9/1992 | Duh et al. |
| 5,188,104 A | 2/1993 | Wernicke et al. |
| 5,217,470 A | 6/1993 | Weston |
| 5,234,454 A | 8/1993 | Bangs |
| 5,246,456 A | 9/1993 | Wilkinson |
| 5,258,015 A | 11/1993 | Li et al. |
| 5,259,399 A | 11/1993 | Brown |
| 5,269,809 A | 12/1993 | Hayhurst et al. |
| 5,292,344 A | 3/1994 | Douglas |
| 5,320,639 A * | 6/1994 | Rudnick .................... 606/213 |
| 5,334,200 A | 8/1994 | Johnson |
| 5,354,271 A | 10/1994 | Voda |
| 5,364,408 A | 11/1994 | Gordon |
| 5,391,182 A | 2/1995 | Chin |
| 5,405,352 A | 4/1995 | Weston |
| 5,423,872 A | 6/1995 | Cigaina |
| 5,428,123 A | 6/1995 | Ward et al. |
| 5,433,723 A | 7/1995 | Lindenberg |
| 5,445,608 A | 8/1995 | Chen et al. |
| 5,470,337 A | 11/1995 | Moss |
| 5,472,446 A | 12/1995 | Torre |
| 5,480,406 A | 1/1996 | Nolan et al. |
| 5,496,311 A | 3/1996 | Abele et al. |
| 5,507,754 A | 4/1996 | Green et al. |
| 5,545,171 A | 8/1996 | Sharkey et al. |
| 5,545,178 A | 8/1996 | Kensey et al. |
| 5,549,621 A | 8/1996 | Bessler et al. |
| 5,554,162 A | 9/1996 | DeLange |
| 5,573,540 A | 11/1996 | Yoon |
| 5,591,177 A | 1/1997 | Lehrer |
| 5,601,604 A | 2/1997 | Vincent |
| 5,626,614 A | 5/1997 | Hart |
| 5,634,936 A | 6/1997 | Linden et al. |
| 5,647,836 A | 7/1997 | Blake, III et al. |
| 5,690,691 A | 11/1997 | Chen et al. |
| 5,716,368 A | 2/1998 | Torre et al. |
| 5,725,557 A | 3/1998 | Gatturna et al. |
| 5,846,254 A | 12/1998 | Schulze et al. |
| 5,888,196 A | 3/1999 | Bonutti |
| 5,931,788 A | 8/1999 | Keen et al. |
| 5,938,669 A | 8/1999 | Klaiber et al. |
| 5,951,590 A | 9/1999 | Goldfarb |
| 5,961,440 A | 10/1999 | Schweich, Jr. et al. |
| 5,971,447 A | 10/1999 | Steck, III |
| 5,993,473 A | 11/1999 | Chan et al. |
| 6,013,053 A | 1/2000 | Bower et al. |
| 6,067,991 A | 5/2000 | Forsell |
| 6,080,160 A | 6/2000 | Chen et al. |
| 6,097,984 A | 8/2000 | Douglas |
| 6,102,922 A | 8/2000 | Jakobsson et al. |
| 6,113,609 A | 9/2000 | Adams |
| 6,143,006 A | 11/2000 | Chan |
| 6,159,234 A * | 12/2000 | Bonutti et al. ................ 606/232 |
| 6,162,234 A | 12/2000 | Freedland et al. |
| 6,186,149 B1 | 2/2001 | Pacella et al. |
| 6,270,530 B1 | 8/2001 | Eldridge et al. |
| 6,420,452 B1 | 7/2002 | Gunatillake et al. |
| 6,437,073 B1 | 8/2002 | Gunatillake et al. |
| 6,447,533 B1 | 9/2002 | Adams |
| 6,454,785 B2 | 9/2002 | De Hoyos Garza |
| 6,475,136 B1 | 11/2002 | Forsell |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,148 B1 | 12/2002 | Pinchuk et al. |
| 6,506,196 B1 | 1/2003 | Laufer |
| 6,511,490 B2 | 1/2003 | Robert et al. |
| 6,535,764 B2 | 3/2003 | Imran et al. |
| 6,558,400 B2 | 5/2003 | Deem et al. |
| 6,656,182 B1 | 12/2003 | Hayhurst |
| 6,663,639 B1 | 12/2003 | Laufer et al. |
| 6,663,647 B2 * | 12/2003 | Reiley et al. .................... 606/192 |
| 6,669,713 B2 | 12/2003 | Adams |
| 6,675,809 B2 | 1/2004 | Stack et al. |
| 6,736,793 B2 | 5/2004 | Meyer et al. |
| 6,746,460 B2 | 6/2004 | Gannoe et al. |
| 6,755,869 B2 | 6/2004 | Geitz |
| 6,773,441 B1 | 8/2004 | Laufer et al. |
| 6,790,213 B2 | 9/2004 | Cherok et al. |
| 6,821,285 B2 | 11/2004 | Laufer et al. |
| 6,835,200 B2 | 12/2004 | Laufer et al. |
| 6,869,395 B2 | 3/2005 | Page et al. |
| 6,900,055 B1 | 5/2005 | Fuller |
| 6,908,487 B2 | 6/2005 | Cigaina |
| 6,981,978 B2 | 1/2006 | Gannoe |
| 6,994,715 B2 | 2/2006 | Gannoe et al. |
| 7,033,373 B2 | 4/2006 | de la Torre et al. |
| 7,037,344 B2 | 5/2006 | Kagan et al. |
| 7,153,314 B2 | 12/2006 | Laufer et al. |
| 7,167,750 B2 | 1/2007 | Knudson et al. |
| 7,223,277 B2 | 5/2007 | DeLegge |
| 7,255,675 B2 | 8/2007 | Gertner et al. |
| 7,310,557 B2 | 12/2007 | Maschino et al. |
| 7,334,822 B1 | 2/2008 | Hines, Jr. |
| 7,338,433 B2 | 3/2008 | Coe |
| 7,354,454 B2 | 4/2008 | Stack et al. |
| 7,374,565 B2 | 5/2008 | Hassler, Jr. et al. |
| 7,402,166 B2 | 7/2008 | Feigl |
| 7,416,554 B2 | 8/2008 | Lam et al. |
| 7,534,248 B2 | 5/2009 | Mikkaichi et al. |
| 7,618,426 B2 | 11/2009 | Ewers et al. |
| 7,666,195 B2 | 2/2010 | Kelleher et al. |
| 7,670,279 B2 | 3/2010 | Gertner |
| 7,695,493 B2 * | 4/2010 | Saadat et al. .................... 606/215 |
| 7,740,647 B2 * | 6/2010 | Mueller .................... 606/232 |
| 7,775,967 B2 | 8/2010 | Gertner |
| 7,841,978 B2 | 11/2010 | Gertner |

(56) References Cited

U.S. PATENT DOCUMENTS

| | | | |
|---|---|---|---|
| 7,850,660 B2 | 12/2010 | Uth et al. | |
| 7,862,546 B2 | 1/2011 | Conlon et al. | |
| 7,875,067 B2 * | 1/2011 | Von Oepen et al. | 623/1.11 |
| 7,988,617 B2 | 8/2011 | Gertner | |
| 2001/0010005 A1 | 7/2001 | Kammerer et al. | |
| 2001/0011543 A1 | 8/2001 | Forsell | |
| 2001/0044639 A1 | 11/2001 | Levinson | |
| 2002/0055757 A1 | 5/2002 | Torre et al. | |
| 2002/0128684 A1 | 9/2002 | Foerster | |
| 2002/0161382 A1 | 10/2002 | Neisz et al. | |
| 2002/0161414 A1 | 10/2002 | Flesler et al. | |
| 2002/0188354 A1 | 12/2002 | Peghini et al. | |
| 2003/0021822 A1 | 1/2003 | Lloyd | |
| 2003/0055463 A1 | 3/2003 | Gordon et al. | |
| 2003/0055465 A1 | 3/2003 | Ben-Haim et al. | |
| 2003/0093117 A1 | 5/2003 | Saadat | |
| 2003/0208212 A1 | 11/2003 | Cigaina | |
| 2004/0006351 A1 | 1/2004 | Gannoe et al. | |
| 2004/0024386 A1 | 2/2004 | Deem et al. | |
| 2004/0030347 A1 | 2/2004 | Gannoe et al. | |
| 2004/0044353 A1 | 3/2004 | Gannoe | |
| 2004/0044357 A1 | 3/2004 | Gannoe | |
| 2004/0054352 A1 | 3/2004 | Adams et al. | |
| 2004/0059289 A1 | 3/2004 | Garza Alvarez | |
| 2004/0068224 A1 | 4/2004 | Couvillon et al. | |
| 2004/0092892 A1 | 5/2004 | Kagan et al. | |
| 2004/0097986 A1 | 5/2004 | Adams | |
| 2004/0098060 A1 | 5/2004 | Ternes | |
| 2004/0116949 A1 | 6/2004 | Ewers et al. | |
| 2004/0122456 A1 | 6/2004 | Saadat et al. | |
| 2004/0122473 A1 | 6/2004 | Ewers et al. | |
| 2004/0148034 A1 | 7/2004 | Kagan et al. | |
| 2004/0186503 A1 | 9/2004 | Delegge | |
| 2004/0193194 A1 | 9/2004 | Laufer et al. | |
| 2004/0194790 A1 | 10/2004 | Laufer et al. | |
| 2004/0243178 A1 | 12/2004 | Haut et al. | |
| 2004/0243179 A1 | 12/2004 | Foerster | |
| 2004/0243180 A1 | 12/2004 | Donnelly et al. | |
| 2004/0260345 A1 | 12/2004 | Foerster | |
| 2004/0267378 A1 | 12/2004 | Gazi et al. | |
| 2005/0022827 A1 | 2/2005 | Woo et al. | |
| 2005/0049718 A1 | 3/2005 | Dann | |
| 2005/0096638 A1 | 5/2005 | Starkebaum et al. | |
| 2005/0159769 A1 | 7/2005 | Alverdy | |
| 2005/0197687 A1 | 9/2005 | Molaei et al. | |
| 2005/0203344 A1 | 9/2005 | Orban, III et al. | |
| 2005/0216040 A1 | 9/2005 | Gertner et al. | |
| 2005/0216042 A1 | 9/2005 | Gertner et al. | |
| 2005/0222638 A1 | 10/2005 | Foley et al. | |
| 2005/0228415 A1 | 10/2005 | Gertner | |
| 2005/0261712 A1 | 11/2005 | Balbierz | |
| 2005/0267405 A1 | 12/2005 | Shah | |
| 2005/0267406 A1 | 12/2005 | Hassler, Jr. | |
| 2005/0267533 A1 | 12/2005 | Gertner | |
| 2005/0267595 A1 | 12/2005 | Chen et al. | |
| 2005/0267596 A1 * | 12/2005 | Chen et al. | 623/23.67 |
| 2005/0277960 A1 | 12/2005 | Hassler, Jr. et al. | |
| 2005/0277974 A1 | 12/2005 | Hassler, Jr. et al. | |
| 2006/0009789 A1 | 1/2006 | Gambale et al. | |
| 2006/0025789 A1 | 2/2006 | Laufer et al. | |
| 2006/0025819 A1 | 2/2006 | Nobis et al. | |
| 2006/0030884 A1 | 2/2006 | Yeung et al. | |
| 2006/0058829 A1 | 3/2006 | Sampson | |
| 2006/0089571 A1 | 4/2006 | Gertner | |
| 2006/0089646 A1 | 4/2006 | Bonutti | |
| 2006/0106288 A1 | 5/2006 | Roth et al. | |
| 2006/0161186 A1 | 7/2006 | Hassler, Jr. et al. | |
| 2006/0161256 A1 | 7/2006 | Ziegler et al. | |
| 2006/0195139 A1 | 8/2006 | Gertner | |
| 2006/0212053 A1 | 9/2006 | Gertner | |
| 2006/0253131 A1 | 11/2006 | Wolniewicz | |
| 2006/0264699 A1 | 11/2006 | Gertner | |
| 2006/0265042 A1 | 11/2006 | Catanese, III et al. | |
| 2006/0276871 A1 | 12/2006 | Lamson et al. | |
| 2006/0282081 A1 | 12/2006 | Fanton et al. | |
| 2007/0027358 A1 | 2/2007 | Gertner et al. | |
| 2007/0049970 A1 | 3/2007 | Belef et al. | |
| 2007/0060940 A1 * | 3/2007 | Brazzini et al. | 606/192 |
| 2007/0073318 A1 | 3/2007 | Carter et al. | |
| 2007/0073323 A1 | 3/2007 | Carter et al. | |
| 2007/0088373 A1 | 4/2007 | Baker | |
| 2007/0112363 A1 | 5/2007 | Adams | |
| 2007/0112385 A1 | 5/2007 | Conlon | |
| 2007/0129738 A1 | 6/2007 | Kraemer et al. | |
| 2007/0167982 A1 | 7/2007 | Gertner et al. | |
| 2007/0173869 A1 | 7/2007 | Gannoe et al. | |
| 2007/0173888 A1 | 7/2007 | Gertner et al. | |
| 2007/0179335 A1 | 8/2007 | Gertner et al. | |
| 2007/0203517 A1 | 8/2007 | Williams et al. | |
| 2007/0233170 A1 | 10/2007 | Gertner et al. | |
| 2007/0235083 A1 | 10/2007 | Dlugos | |
| 2007/0239284 A1 | 10/2007 | Skerven et al. | |
| 2007/0250103 A1 | 10/2007 | Makower | |
| 2007/0255308 A1 | 11/2007 | Williams et al. | |
| 2007/0260259 A1 | 11/2007 | Fanton et al. | |
| 2007/0270892 A1 | 11/2007 | Makower et al. | |
| 2007/0276293 A1 | 11/2007 | Gertner | |
| 2007/0276432 A1 | 11/2007 | Stack et al. | |
| 2008/0009888 A1 | 1/2008 | Ewers et al. | |
| 2008/0015501 A1 | 1/2008 | Gertner | |
| 2008/0033488 A1 | 2/2008 | Catanese, III et al. | |
| 2008/0039894 A1 | 2/2008 | Catanese, III et al. | |
| 2008/0051823 A1 | 2/2008 | Makower | |
| 2008/0051824 A1 | 2/2008 | Gertner | |
| 2008/0051850 A1 | 2/2008 | Sparks et al. | |
| 2008/0058710 A1 | 3/2008 | Wilk | |
| 2008/0071306 A1 | 3/2008 | Gertner | |
| 2008/0082113 A1 | 4/2008 | Bishop et al. | |
| 2008/0086082 A1 | 4/2008 | Brooks | |
| 2008/0086172 A1 | 4/2008 | Martin et al. | |
| 2008/0091220 A1 | 4/2008 | Chu | |
| 2008/0091237 A1 | 4/2008 | Schwartz et al. | |
| 2008/0109027 A1 | 5/2008 | Chen et al. | |
| 2008/0147002 A1 | 6/2008 | Gertner | |
| 2008/0161717 A1 | 7/2008 | Gertner | |
| 2008/0167519 A1 | 7/2008 | St-Germain | |
| 2008/0167647 A1 | 7/2008 | Gertner | |
| 2008/0167648 A1 | 7/2008 | Gertner | |
| 2008/0172074 A1 | 7/2008 | Baker et al. | |
| 2008/0172079 A1 | 7/2008 | Birk | |
| 2008/0208240 A1 * | 8/2008 | Paz | 606/191 |

FOREIGN PATENT DOCUMENTS

| | | |
|---|---|---|
| EP | 1 602 392 A1 | 7/2005 |
| EP | 1 591 140 A1 | 11/2005 |
| EP | 1 547 642 B1 | 8/2007 |
| EP | 1 607 071 B1 | 8/2007 |
| EP | 1 884 198 A2 | 2/2008 |
| EP | 1 884 199 A1 | 2/2008 |
| EP | 1 670 361 B1 | 4/2008 |
| EP | 1670361 | 4/2008 |
| FR | 2907665 | 11/2008 |
| WO | WO 87/00034 | 1/1987 |
| WO | WO 99/25418 | 5/1999 |
| WO | WO 9925418 | 5/1999 |
| WO | WO 0009049 | 2/2000 |
| WO | WO 0018330 | 4/2000 |
| WO | WO 00/74573 A1 | 12/2000 |
| WO | WO 0147435 | 7/2001 |
| WO | WO 0235980 | 5/2002 |
| WO | WO 02071951 | 9/2002 |
| WO | WO 030055420 | 7/2003 |
| WO | WO 03095015 | 11/2003 |
| WO | WO 2004004542 | 1/2004 |
| WO | WO 2004014237 | 2/2004 |
| WO | WO 2004019765 | 3/2004 |
| WO | WO 2004021894 | 3/2004 |
| WO | WO 2004037064 | 5/2004 |
| WO | WO 2005007232 | 1/2005 |
| WO | WO 2005009288 | 2/2005 |
| WO | WO 2005/018417 A2 | 3/2005 |
| WO | WO 2005/018417 A3 | 3/2005 |
| WO | WO 2005018417 | 3/2005 |

(56) References Cited

FOREIGN PATENT DOCUMENTS

| | | |
|---|---|---|
| WO | WO 2005020802 | 3/2005 |
| WO | WO 2005/094447 A2 | 10/2005 |
| WO | WO 2006020370 | 2/2006 |
| WO | WO 2006/049725 A2 | 5/2006 |
| WO | WO 2006063593 A2 | 6/2006 |
| WO | WO 2006108203 | 10/2006 |
| WO | WO 2006127431 | 11/2006 |
| WO | WO 2006134106 A1 | 12/2006 |
| WO | WO 2007017880 A2 | 2/2007 |
| WO | WO 2007/067206 A2 | 6/2007 |
| WO | WO 2007064906 A2 | 6/2007 |
| WO | WO 2007/110866 A2 | 10/2007 |
| WO | WO 2007074573 | 12/2007 |
| WO | WO 2008/006084 A2 | 1/2008 |
| WO | WO 2008006084 | 1/2008 |
| WO | WO 2008006084 A2 | 1/2008 |
| WO | WO 2008013814 | 1/2008 |
| WO | WO 2008043044 A2 | 4/2008 |

OTHER PUBLICATIONS

Buchwald—Overview of Bariatric Surgery. Journal of the American College of Surgeons, pp. 367-375, Mar. 2002.

Sharp, et al., The 4-S Modification of the Roeder Knot: How to Tie It. pp. 1004-1006, vol. 90, No. 6, Dec. 1997.

Schauer, et al., New application for Endoscopy: the emerging field of endoluminal and transgastric bariatric surgery. 10 pgs., Apr. 24, 2006.

Buchwald et al., "Bariatruc Surgery: A Systematic Review and Meta-analysis", JAMA 2004, vol. 292, No. 14, pp. 1724-1737.

Buchwald et al., "Evolution of Operative Procedures for the Management of Morbid Obesity 1950-2000", Obesity Surgery 2002, 12:705-717.

Camerini et al., "Thirteen Years to Follow-up in Patients with Adjustable Silicone Gastric Banding for Obesity: Weight Loss and Constant Rate of Late Specific Complications" Obesity Surgery 2004, 14:1343-1348.

Cope et al., "Percutaneous Transgastric Technique for Creating Gastroenteric Anastomoses in Swine", Journal of Vascular and Interventional Radiology, 2004, 15:177-181.

Cummings et al., "Genetics and Pathophysiology of Human Obesity", An Annual Review of Medicine, 2003, 54:453-471/.

Johnston et al., "The Magenstrasse and Mill Operation for Morbid Obesity", Obesity Surgery 2003, 13:10-16.

Morino et al., "Laparoscopic Adjustable Silicone Banding Versus Vertical Banded Gastroplasty in Morbidly Obese Patients" Analysis Obesity Surgery vol. 238, No. 6, 2003, pp. 835-842.

Roman et al., "Intragastric Balloon of Non-Morbid Obesity: A Retrospective Evaluaton of Tolerance and Efficacy", Obesity Surgery, 2004, 14:539-544.

Sallet et al., Brazillian Mulitcenter Study of the Intragastric Ballon; Obesity Surgery, 2004, 14, pp. 991-998.

Sjostrom et al., Lifestyle, Diateters, and Cardiovascular Risk Factors 10 years after Bariatric Surgery, New England Journal of Medicine, 2004, 351, (6) 2683-2693.

Smith et al., "Modification of the Gastric Partitioning Operation for Morbid Obesity", Am. J. Surgery 142, Dec. 1981.pp. 725-730.

Smith et al., "Results and Complication of Gastric Partitioning: Four Years Follow-Up of 300 Morbidly OBese Patients", The American Journal of Surgery, 1983, (146) pp. 815-819.

Trumble et al., "Method for measuring long-term function of muscle-powered implants via radiotelemetry" J. Appl. Physiol. 2001,90: pp. 1977-1985.

About the Vertical Sleeve Gastrectomy. Mar. 24, 2006, pp. 1-1. http://obesityhelp.com/forums/VSG/about.html.

Akira., JP63277063, Japanese and English Abstract, Nov. 15, 1988, pp. 1-4.

Abhyankar et al, Use of a tissue expander and a polyglactic acid (Vicryl) mesh to reduce radiation enteritis: case report and literature view, 21: pp. 755-757, Aug. 2005.

Buchwald, Overview of Bariatric Surgery, vol. 194, No. 3, Mar. 2002, pp. 367-375.

Burnett, et al., The Use of a Pelvic Displacement Prosthesis to Exclude the Small Intestine from the Radiation Field Following Radical Hysterectomy, 79, pp. 438-443, 2000. http://www.idealibrary.com.

Brolin, Robert E., Gastric Bypass. vol. 81, No. 5, Oct. 2001, pp. 1077-1095.

Cheng, Splenic Epidermoid Cyst, pp. 1-3, 1997.

Med-4840, Product Profile , Mar. 30, 2007, pp. 1-2.

DeMaria, Eric J., Laparoscopic Adjustable Silicone Gastric Banding. vol. 81, No. 5, Oct. 2001, pp. 1129-1143.

Deitel,Mervyn., Overview of Operations for Morbid Obesity. vol. 22, No. 9, Sep. 1998, pp. 913-918.

Doherty, Cornelius., Technique of Vertical Banded Gastroplasty. vol. 81, No. 5, Oct. 2001, pp. 1097-1111.

Foglia et al., Management of giant omphalocele with rapid creation of abdominal domain, 41, pp. 704-709, 2006.

Fried et al., Physical Principles of Available Adjustable Gastric Bands: How they Work. Obesity Surgery, 14, 2004, pp. 1118-1122.

Gertner MD, Stomach Restriction with an Extragastric Balloon, pp. 1, Abstract for 2007.

Geliebter et al; Extra-abdominal pressure alters food intake, intragastric pressure, and gastric emptying rate. 1986, pp. R549-R552.

Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, pp. 473-483, No. 7, vol. 60, Jul. 1994.

Hainaux et al., Laparoscopic adjustable silicone gastric banding: radiological appearances of a new surgical treatment for morbid obesity. 1999, Abdom Imaging 24: 533-537.

Konturek et al., Neuro-Hormonal Control of Food Intake; Basic Mechanisms and Clinical Implications, 2005, 56, Supp 6, 5-25. www.jpp.krakow.pl.

Lam et al., Huge Splenic Epidemoid Cyst: A Case Report, 1997; 60:113-6.

Laparoscopic Duodenal Switch, Mar. 24, 2006, http://wo-pub2.med.cornell.edu/chi.bin/WebObjects/PublicA.woa/5/w . . . p. 1-1.

Lee et al., Laparoscopic Vertical Sleeve Gastrectomy: A Novel Bariatric Procedure-superior to Estabilished Operations? pp. 1-27. 90th Annual Clinical Congress, New Orleans, LA, Oct. 10, 2004.

Malassagne, et al., Intra-abdonimal Sengstaken-Blakemore tube Placement for acute venous outflow obstruction in reduced-size Liver, Nov. 1996, 83, pp. 1086.

Marceau, et al., Malabsorptive Obesity Surgery. vol. 81, Oct. 2001, No. 5, pp. 1113-1127.

Mera, et al., Use of the Breast Implant for Liver Graft Malposition. vol. 5, No. 6, Nov. 1999, pp. 534-535.

Obesity Surgery Including Laparoscopy and Allied Care. vol. 16, No. 1, Jan. 2006, pp. 1-2. www.obesitysurgey.com.

Pomerri et al., Adjustable Silicone Gastric Banding of Obesity. , 1992, Gastrointest Radiol 17:207-210.

Schauer, et al., New applications for endoscopy: the emerging field of endoluminal and transgastric bariatric surgery, DOI:10.1007/s00464-006-9008-8, 2006.

The Sleeve Gastrectomy (or 2-Stage Procedure). 2006, pp. 1-2. http://surgicallyslim.com/sleeve.htm.

Walker, et al. Bladder Augmentation in Dogs Using the Tissue Capsule Formed Around a Perivesical tissue Expander, vol. 168, pp. 1534-1536, 2002.

Zwart et al., Gastric Motility: Comparison of Assessement with Real-Time MR Imaging or Barostat Experience1., 224: pp. 592-597, Aug. 2002.

Tucker, Diana, Medical Device Daily. vol. 10, No. 102, pp. 1-10, May 26, 2006.

\* cited by examiner

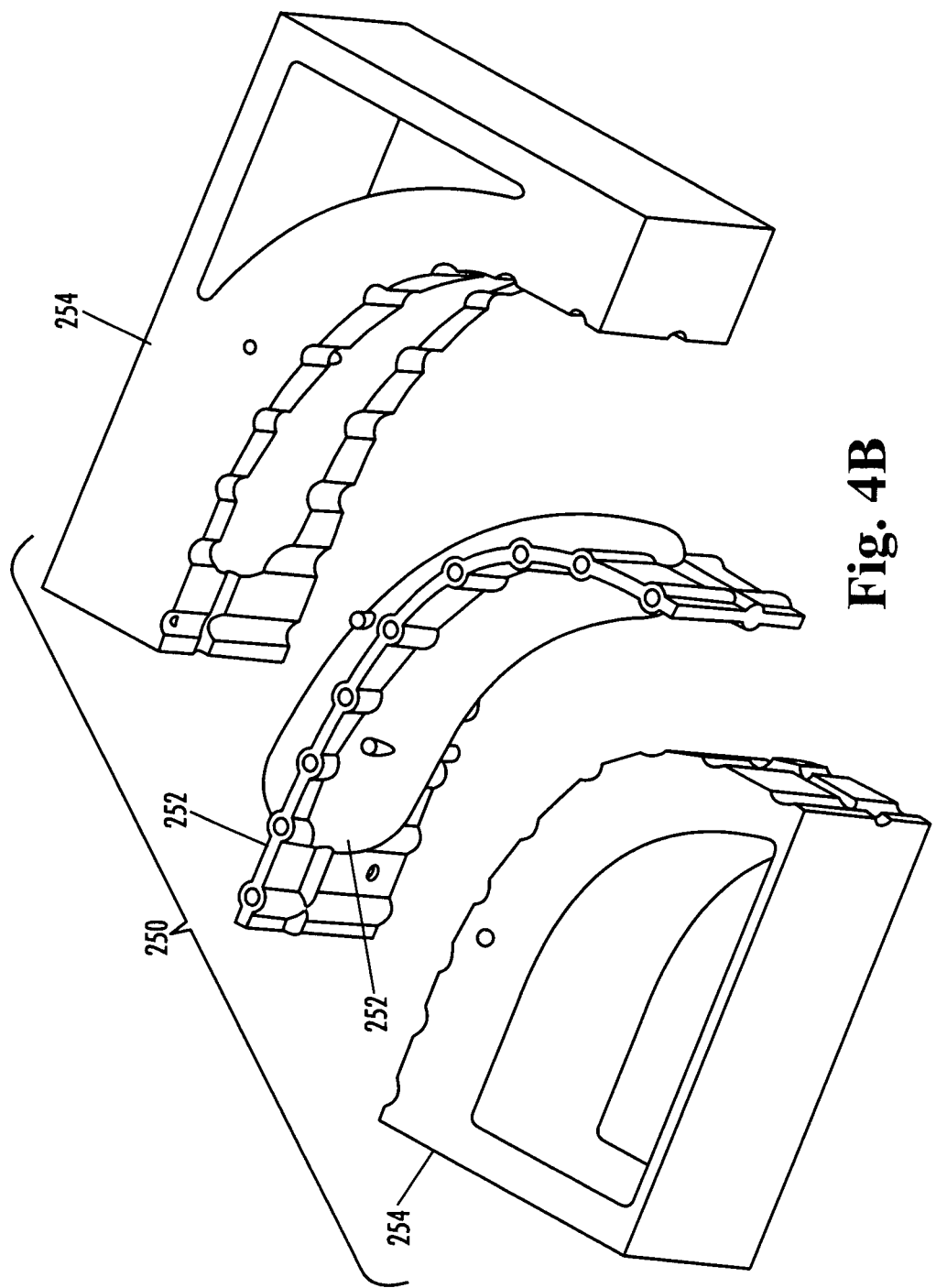

| NAME | SIZE | MINI Vol (cc) | TARGET Vol (cc) | MAX Vol (cc) |
|---|---|---|---|---|
| A-short | 2 | 450 | 800 | 1200 |
| A-long | 1 | 550 | 975 | 1462 |
| B-short | 4 | 635 | 1125 | 1687 |
| B-long | 3 | 735 | 1300 | 1950 |

| NAME | SIZE | MINI | | TARGET | | MAX | |
|---|---|---|---|---|---|---|---|
| | | Vol (cc) | | Vol (cc) | | Vol (cc) | |
| A-short | 2 | FOAM: 181<br>SALINE: 269 | TOTAL: 450 | FOAM: 181<br>SALINE: 619 | TOTAL: 800 | FOAM: 181<br>SALINE: 1019 | TOTAL: 1200 |
| A-long | 1 | FOAM: 235<br>SALINE: 315 | TOTAL: 550 | FOAM: 235<br>SALINE: 740 | TOTAL: 975 | FOAM: 235<br>SALINE: 1227 | TOTAL: 1462 |
| B-short | 4 | FOAM: 243<br>SALINE: 392 | TOTAL: 635 | FOAM: 243<br>SALINE: 882 | TOTAL: 1125 | FOAM: 243<br>SALINE: 1444 | TOTAL: 1687 |
| B-long | 3 | FOAM: 292<br>SALINE: 443 | TOTAL: 735 | FOAM: 292<br>SALINE: 1008 | TOTAL: 1300 | FOAM: 292<br>SALINE: 1658 | TOTAL: 1950 |

Fig. 10

DEVICES AND METHODS FOR TREATMENT OF OBESITY

FIELD OF THE INVENTION

The present invention relates to treatment of obesity, more particularly to implantable devices and methods of implanting the devices in the abdominal cavity to treat an obese patient.

BACKGROUND OF THE INVENTION

Obesity has become a major health concern, both nationally and internationally. The National Center for Health Statistics (NCHS) estimates that over 120 million Americans are overweight, including about 56% of the adult population. Of these, about 52 million are considered obese, as measured by a body mass index (BMI) of 30 or greater. In Europe, an estimated 77 million people are obese, as measured by the same standard. This problem is not limited to western nations, as many developing countries are reported to have obesity rates over 75% of the adult population.

Co-morbidities that are associated with obesity include, but are not limited to type II Diabetes, high blood pressure, sleep apnea, stroke and arthritis, the symptoms of which often tend to be lessened or alleviated upon loss of weight by a person so affected.

In the U.S., options for treatment of obesity are currently quite limited. Current treatment methodologies typically rely upon surgically introducing a "malabsorptive" environment in the gastro-intestinal tract, a restrictive environment, or a combination of these. One available treatment method is gastric bypass surgery and another is referred to as gastric banding (one of these techniques is referred to as the LAP-BAND™ procedure). These procedures are limited to only those patients with a BMI over 40 (or over 35, with co-morbidities present).

Gastric bypass procedures incur a great deal of morbidity and create a malabsorptive state in the patient by bypassing a large portion of the intestines. Serious side effects, such as liver failure have been associated with this procedure, as well as chronic diarrhea. Another surgical procedure that has a high degree of morbidity associated with it is known as the "Gastric Bypass Roux-en-Y" procedure. This procedure reduces the capacity of the stomach by creating a smaller stomach pouch. The small space holds only about one ounce of fluid. A tiny stomach outlet is also surgically created to slow the speed at which food leaves the stomach. Staples are used to create a small (15 to 20 cc) stomach pouch, with the rest of the stomach being stapled completely shut and divided from the stomach pouch. The small intestine is divided just beyond the duodenum, brought up, and connected to the newly formed stomach pouch. In addition to the considerable morbidity associated with this procedure, other disadvantages include "dumping syndrome", where stomach contents are literally "dumped" rapidly into the small intestine which may lead to nausea, weakness, sweating, faintness, and diarrhea; hernias resulting from the surgery; gallstones; leakage of the connection between the pouch and the intestine; stretching of the pouch that was formed; nutritional deficiencies; and possible dehiscence of the staples.

The LAPBAND™ is a band that, when placed, encircles the fundus-cardia junction and is inflatable to constrict the same. It does not reduce the volume of the stomach, but rather restricts passage of food into the stomach, the theory being that the patient will feel satiety with a much smaller volume of food than previously. Although the LAPBAND™ procedure is less invasive than a gastric bypass procedure, it also typically achieves less weight loss. Further, it is not a simple procedure and requires a substantial amount of training by a surgeon to become proficient in performing the procedure. Also, a substantial amount of dissecting and suturing is required because the pathway by which the band is introduced is not an existing pathway, and must be established by dissection. Great care is required to avoid blood vessels and nerves that may be in the intended pathway to be created by the dissection. After placing the band around the fundus-cardia junction, the ends of the band must be connected together and then it must be cinched down into place. Additionally, complications such as erosion at the fundus-cardia junction, slippage of the band from its intended location, nausea/vomiting, gastroesophageal reflux, dysphagia and lack of effectiveness in causing weight loss have been reported.

Intragastric balloons have also been placed, in an attempt to fill a portion of the volume in the stomach, with the theory being that it will then require less food than previously, to give the patient a sensation of fullness or satiety. This procedure involves delivery of a balloon (typically, transorally) to the interior of the stomach and inflation of the balloon to take up a portion of the volume inside the stomach. However, intragastric balloons may also lead to complications such as obstruction, vomiting and/or mucosal erosion of the inner lining of the stomach. The balloon can break down over extended exposure to the stomach's acids, and in some cases, after breaking down, the balloon translated through the intestines and caused a bowel obstruction.

Gastrointestinal sleeves have been implanted to line the stomach and/or a portion of the small intestines to reduce the absorptive capabilities of the small intestine and/or to reduce the volume in the stomach, by reducing the available volume to the tubular structure of the graft running therethrough. Although weight loss may be effective while these types of devices are properly functioning, there are complications with anchoring the device within the stomach/GI tract, as the stomach and GI tract function to break down things that enter into them and to move/transport them through. Accordingly, the integrity of the anchoring of the device, as well as the device itself may be compromised over time by the acids and actions of the stomach and GI tract.

A sleeve gastrectomy is an operation in which the left side of the stomach is surgically removed. This results in a much reduced stomach which is substantially tubular and may take on the shape of a banana. This procedure is associated with a high degree of morbidity, as a large portion of the stomach is surgically removed. Additionally, there are risks of complications such as dehiscence of the staple line where the staples are installed to close the surgical incisions where the portion of the stomach was removed. Further, the procedure is not reversible.

In the laparoscopic duodenal switch, the size of the stomach is reduced in similar manner to that performed in a sleeve gastrectomy. Additionally, approximately half of the small intestine is bypassed and the stomach is reconnected to the shortened small intestine. This procedure suffers from the same complications as the sleeve gastrectomy, and even greater morbidity is associated with this procedure due to the additional intestinal bypass that needs to be performed. Still further, complications associated with malabsorption may also present themselves.

An inflatable gastric device is disclosed in U.S. Pat. No. 4,246,893, in which a balloon is inserted anteriorly of the stomach and posteriorly of the left lobe of the liver. The balloon is then inflated to compress the stomach so that it fills with less food that would ordinarily be possible. Not only does this device compress the stomach, but it also compresses the liver, as seen in FIG. 5 of the patent, which may cause complications with the liver function. Additionally, the balloon is simply placed into this location, and there is no assurance that it will not migrate and lose its effectiveness in compressing the stomach to the degree intended. Still further, the balloon is of a simple spherical design, and, as such, extends pressure outwardly in all directions, 360 degrees, in all planes. Accordingly, the liver is compressed just as much as the stomach is. Also, the compression forces against the stomach are not ideal, as the spherical balloon conformation does not match the conformation of the expanding stomach. The stomach is not spherical when expanded, or concave with a constant radius of curvature, but expands into a designated space that allows the fundus to expand preferentially more than other parts of the stomach.

Brazzini et al. in WO2005/18417 discloses at least two or more expandable devices used to treat obesity, in which the devices are inserted through the abdominal wall and anchored against the external surface of the stomach wall by an anchoring mechanism that extends through the stomach wall and fixes to the internal surface of the stomach wall.

U.S. Patent Publication No. 2005/0261712 to Balbierz et al. describes capturing a device against the outer surface of the stomach wall to form a restriction that appears to function similarly to the restriction imposed by the LAPBAND™. The anchoring of the devices disclosed relies upon placement of features against the internal wall of the stomach to form an interlock with the device which is placed against the external wall of the stomach.

U.S. Patent Publication Nos. 2005/0267533 and 2006/0212053 to Gertner disclose devices for treatment of obesity that use one or more anchoring mechanisms that are passed through the wall of the stomach to establish an anchor.

U.S. Pat. No. 6,981,978 to Gannoe discloses devices for reducing the internal cavity of the stomach to a much smaller volume, which may be used to carry out a bypass procedure. Stapling is employed to isolate the smaller volume in the stomach, and thus the same potential disadvantages are present as with other stapling procedures described herein.

U.S. Pat. No. 6,186,149 to Pacella et al. describes an occluder device that can be used as a dietary control device (see FIG. 8C). The occluder device is placed against the wall of the stomach and inflated to press inwardly on the stomach wall. A frame is wrapped around the stomach wall and is inflated to press against the stomach wall. However, there is no disclosure of how the frame might be adjusted to maintain a position relative to the stomach wall as the size of the stomach varies.

Gastric reduction techniques have been attempted, such as by inserting instruments trans-orally and reducing the volume of the stomach by stapling portions of it together. However, this technique is prone to failure due to the staples pulling through the tissues that they are meant to bind.

Techniques referred to as gastric pacing endeavor to use electrical stimulation to simulate the normal feedback mechanisms of a patient that signal the brain that the patient is full, or satiated. While these techniques are less invasive than some of the other existing treatments, statistics to date have shown that the amount of weight lost by using such techniques is less than satisfactory.

Currently marketed drugs for weight loss, such as XENICAL®, MERIDIA® and Phen fen have largely failed, due to unacceptable side effects and complications, and sometimes to an ineffective amount of weight loss. Other drugs that are on the horizon include ACCOMPLIA® and SYMLIN®, but these are, as yet, unproven.

The risk and invasiveness factors of currently available surgeries are often too great for a patient to accept to undergo surgical treatment for his/her obesity. Accordingly, there is a need for less invasive, yet effective surgical treatment procedures for morbidly obese patients (patients having a BMI of 35 or greater). Also, since the current surgical procedures are currently indicated only for those patients having a BMI of 40 or greater, or 35 or greater when co-morbidities are present, it would be desirable to provide a surgical procedure that would be available for slightly less obese patients, e.g., patients having a BMI of 30 to 35 who are not indicated for the currently available surgical procedures. It would further be desirable to provide a surgical procedure that would be indicated for obese patients having a BMI in the range of 30-35, as well as for more obese patients.

SUMMARY OF THE INVENTION

The present invention provides methods, devices and tools for treating a patient to assist with weight loss. One device embodiment includes a fillable member configured to be positioned exteriorly of the stomach in an abdominal cavity of the patient. The fillable member is configured to be filled after placement of the device in the abdominal cavity, wherein the device, with the fillable member in a filled configuration, has a buoyancy characteristic comprising a density of about 900 kg/m3 to about 1100 kg/m3.

In at least one embodiment, a buoyancy member exhibiting substantially uniform density throughout is provided, wherein the density of the buoyancy member is less than a density of the fillable member when the fillable member is filled with a liquid, such that, when the buoyancy member is combined with the fillable member in the filled configuration, the density of the device is less than the density of the fillable member when filled with a liquid and not combined with the buoyancy member.

In at least one embodiment, the buoyancy member is non-expandable.

In at least one embodiment, the buoyancy member comprises porous silicone.

In at least one embodiment, the device further includes at least one attachment member extending out from a surface of the fillable member.

In at least one embodiment, the attachment member includes tissue ingrowth-enhancing material thereon.

A method of treating a patient is provided including the steps of: taking at least one internal measurement in the abdominal space of the patient; and selecting an appropriately sized device for implantation into the abdominal cavity of the patient, based on the internal measurements taken.

In at least one embodiment, the selecting comprises: referencing a chart that correlates internal measurements with device sizes; and selecting a device size from the chart based on the internal measurements taken.

In at least one embodiment, the selecting comprises: ordering a custom-sized device sized specifically for the internal measurements taken.

In at least one embodiment, the appropriately sized device is selected from a plurality of devices having a plurality of different sizes, each of the devices comprising a fillable member, wherein each fillable member, when filled to an filled configuration has at least a different length or diameter dimension different from those of the other fillable members when filled a corresponding amount.

In at least one embodiment, the method further includes the steps of: passing the selected device into the abdominal cavity of the patient, wherein the device includes at least one attachment member extending from a main body portion thereof; and at least temporarily attaching the at least one attachment member to an internal abdominal structure, without attachment to the stomach.

In at least one embodiment, the method further includes at least partially filling the main body portion with a fluid, using an adjustment aid tool that does not require a pushing pressure against the hand of the user to deliver the fluid out of the syringe In at least one embodiment, the method further includes: placing a volume occupying member of the device exteriorly of the stomach and into the abdominal cavity of the patient adjacent the stomach to prevent expansion of the stomach into a volume occupied by the placed device; and attaching an attachment member connected to the volume occupying member to at least one internal abdominal structure, without attachment to the stomach; wherein at least a portion of the attachment member is configured to encourage tissue ingrowth from the at least one internal abdominal structure that it is attached to.

In at least one embodiment, the attachment member is attached to the abdominal wall of the patient.

In at least one embodiment, the attaching includes passing at least one suture through the abdominal wall, and fixing the at least one suture externally of an external surface of the abdominal wall.

In at least one embodiment, the attaching includes puncturing through a location of the abdominal wall above a location of at least one the suture and inserting an instrument into the abdominal cavity; capturing the suture; and wherein the passing at least one suture through the abdominal wall comprises pulling a portion of the at least one suture through the abdominal wall; applying tension to the at least one suture to draw the at least one attachment tab against an internal surface of the abdominal wall; and fixing the at least one suture externally of the abdominal wall.

In at least one embodiment, the method further includes placing a suture placement template over the skin of the patient in an orientation to align at least one location over the abdominal wall through which the puncturing through a location of the abdominal wall is conducted, prior to the puncturing through the location of the abdominal wall.

In at least one embodiment, the placing includes delivering the device through a small opening through the abdominal wall of the patient and a tract leading through the abdominal wall.

In at least one embodiment, the placing includes passing the device through a small opening in the patient's abdominal wall, wherein the fillable member is in a collapsed configuration during the passing, and wherein the fillable member is filled to a fill configuration in a space in the abdominal cavity external of the stomach to perform at least one of: prevention of expansion of the stomach of the patient into the space; and compression of a portion of the stomach.

In at least one embodiment, the fillable member is filled to a mini volume fill configuration upon the placing, where the fillable member in the mini volume fill configuration has no wrinkles upon the placing, the method further comprising subsequently filling the fillable member to a target volume fill configuration.

In at least one embodiment, the fillable member is left in the mini volume fill configuration upon completion of implantation of the device, and wherein the fillable member is filled to the target volume fill configuration after a period of time has elapsed to allow tissue ingrowth into the attachment member.

In at least one embodiment, the attaching includes puncturing through a location of the abdominal wall above a location of at least one suture, having been preinstalled through the attachment member, and inserting an instrument into the abdominal cavity; capturing the at least one suture; pulling a portion of the at least one suture through the abdominal wall; applying tension to the at least one suture to draw the attachment member against an internal surface of the abdominal wall; and fixing the at least one suture externally of the abdominal wall.

In at least one embodiment, the placing includes placing a volume occupying member of the device using a tool comprising: a delivery tube dimensioned to receive the volume occupying member in a compact configuration with the volume occupying member in a compressed configuration; a plunger configured to be received in an annulus of the tube; a plunger shaft extending proximally from the plunger, the plunger shaft having a length sufficient to extend a handle at a proximal end of the plunger shaft out of a proximal end of the tube when the plunger is flush or nearly flush with a distal end of the tube; and a mandrel fixed relative to the plunger shaft and extending distally of the plunger, the mandrel being receivable through the annulus along with the plunger.

In at least one embodiment, the tool further includes a tether fixed with respect to the plunger shaft, the tether having sufficient length to extend distally of a distal end of the mandrel; and a sheath dimensioned to wrap around the volume occupying member the volume occupying member is in the compact configuration.

These and other features of the invention will become apparent to those persons skilled in the art upon reading the details of the devices, kits, tools and methods as more fully described below.

BRIEF DESCRIPTION OF THE DRAWINGS

FIGS. 4A-4C show various views of a mold that can be used to form an expanded polymer product exhibiting substantially uniform density throughout and for use as a buoyancy member according to the present invention.

FIG. 10 is a chart that illustrates the relative volume of the buoyancy member and the liquid (in this case, saline) volume contained in the fillable members at the various min, target and max volumes.

DETAILED DESCRIPTION OF THE INVENTION

Figure 1:
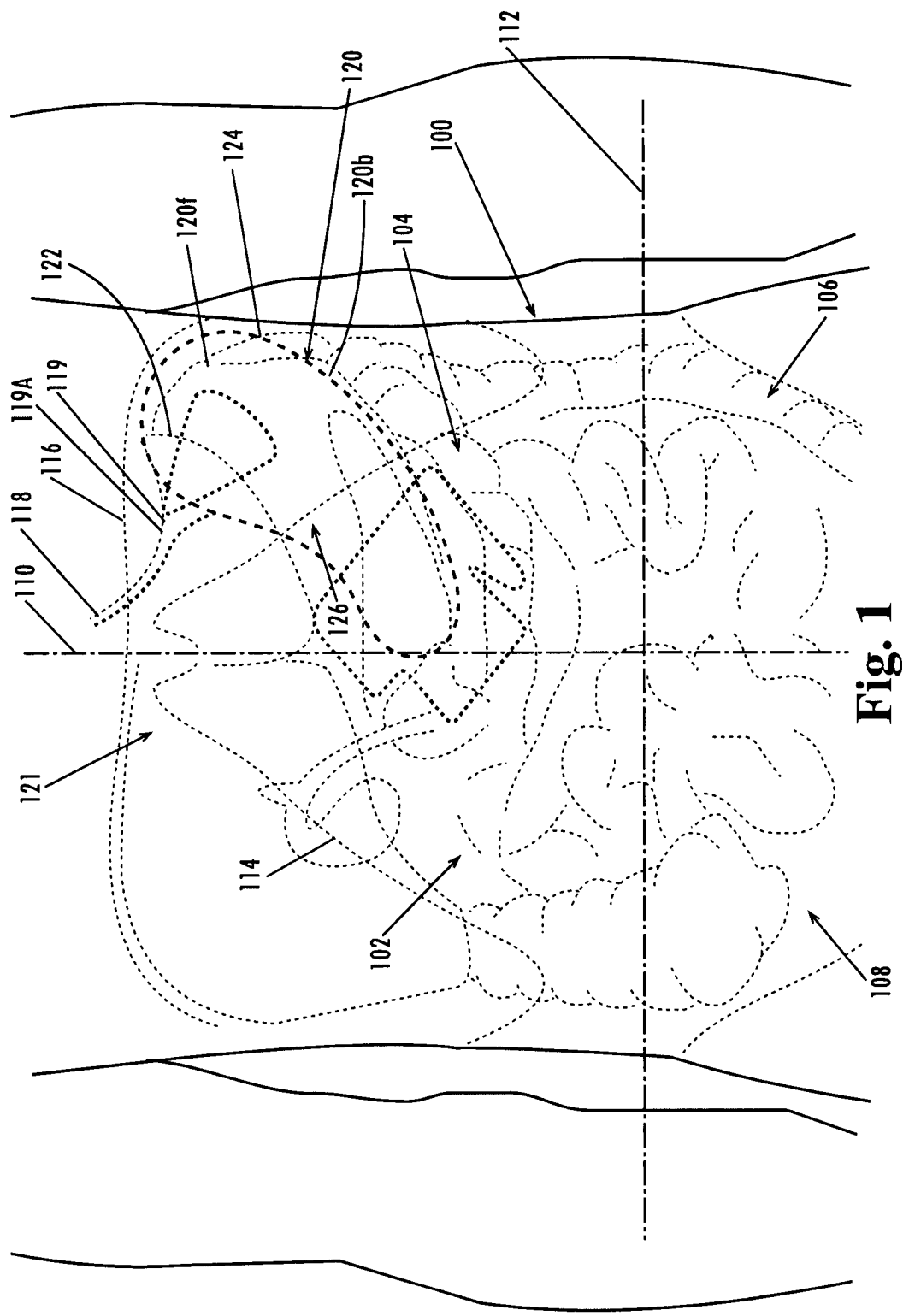
FIG. 1 illustrates the anatomy of the abdominal cavity and its contents, and surrounding features.

Before the present devices, methods and instruments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

It must be noted that as used herein and in the appended claims, the singular forms "a", "an", and "the" include plural referents unless the context clearly dictates otherwise. Thus, for example, reference to "a fillable member" includes a plurality of such fillable members and reference to "the joint" includes reference to one or more joints and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The "wall" of the stomach refers to all of the layers that make up the stomach wall, including the mucosa, submucosa, muscular layers and serosa. A "layer", "layer of the stomach wall" or "stomach wall layer" refers to a mucosal layer, submucosal layer, muscular layer or serosal layer.

A "proximal" end of an instrument is the end that is nearer the surgeon when the surgeon is using the instrument for its intended surgical application.

A "distal" end of an instrument is the end that is further from the surgeon when the surgeon is using the instrument for its intended surgical application.

An "internal body structure" when referred to as a structure to which a device is to be anchored, refers to a structure internal to the skin of a patient, and which can be within the abdominal cavity of the patient, or just outside of it, such as including the outer surface of a wall that partially defines the abdominal cavity. Structures to which a device can be anchored include, but are not limited to: one or more ribs, the intercostal muscles, the abdominal surface of the diaphragm, the stomach (but where the anchor does not pass through the wall of the stomach), the anterior abdominal wall, the posterior abdominal wall and the lateral abdominal wall, the esophagus, the angle of his in the stomach, the gastro-intestinal junction, the gastro-esophageal junction, the columnar ligaments of the diaphragm near the gastro-esophageal junction, the superior aspect of the omentum, peritoneum, liver, connective tissues, ligaments, and blood vessels.

An "internal abdominal structure" refers to an internal body structure that is within the abdominal cavity of the patient, including the abdominal wall. For example, attachment to an inner wall surface of the abdominal wall is an attachment to an internal abdominal structure.

The devices of the present invention are designed to prevent the possible issue of erosion caused by a volume-reducing member outside of the stomach in the abdominal cavity that reduces the ability of the stomach to expand, by not requiring anchoring of the member to the stomach, but by fixing the member to another intra-abdominal structure. By allowing the stomach to move freely in the remaining volume not occupied by the volume-reducing member, the stomach's possible expansion size will be decreased, but there will be less opportunity for the formation of pressure necrosis since no one region will be subjected to concentrated forces. With the device in place, there is substantially no distensibility of the stomach as normally exists with an unconstrained stomach. With distensibility restricted and gastric volume reduced, as the patient ingests food, the intra-gastric pressure will rise to a level sufficient to produce satiety without distension or volume expansion of one or more regions of the stomach. The device occupies so much volume outside of the stomach in the abdominal cavity that the stomach does not substantially depart from the shape set by the device even when filled with food. Another physiological benefit of the device is that the stomach's ability to relax in response to ingestion of food is reduced or eliminated, through producing earlier satiety.

One additional physiological benefit of the volume-reducing member may further be to substantially reduce the actual volume of the stomach itself, remodeling the organ as the muscle contracts into its new shape over the period of weeks or months (just as the heart remodels when constrained from over-expansion). Remodeling the stomach allows the volume-reducing member to be implanted temporarily. The preferred embodiments also are positioned in a location to substantially fill the space normally occupied by the fundus, thus moving the stomach medially and wedging the stomach between the volume-reducing member and the medial and anterior aspects of the liver, and the spine posteriorly. This position also ensures that the volume-reducing member is almost entirely maintained underneath the diaphragmatic umbrella beneath the ribs on the left side, thus concealing the volume-reducing member, and preventing it from producing an unsatisfactory cosmetic result. Further, the preferred embodiments can have elements for anchoring on one or more locations along the abdominal cavity wall to prevent migration. Further, the preferred embodiments are provided with an outer surface that is very atraumatic. Embodiments described may include at least one fillable member, preferably a fillable member, made of a material or material composite that is impermeable to fluid, which may be substantially impermeable to gas and is at least impermeable to liquid, a foam member which adds buoyancy to the device. For example, a buoyancy member may be included with a liquid-filled fillable member of a device, that by itself, has negative buoyancy, so that the buoyancy member provides positive buoyancy to bring the combined buoyancies of these components of the device nearer to a neutral buoyancy, when implanted outside of the stomach in the abdominal cavity of a patient. It can be beneficial to make the combined buoyancy slightly positive in the abdominal cavity to help prevent the device from migrating down in the patient.

The devices described herein can be provided as versatile devices. For example, the same device with a fillable member can be implanted and attached via a laparoscopic surgical procedure, an oral trans-gastric procedure, or a variation of percutaneous procedures in which non general anesthesia and little or no insufflation are used. The device can be implanted and anchored directly to at least one internal abdominal structure, or alternatively, can be implanted by fixing to an anchoring frame having been anchored to at least one internal abdominal structure.

Abdominal Cavity Anatomy

FIG. 1 illustrates the anatomy of the abdominal cavity and its contents, and surrounding features. The abdominal cavity 100 is shown divided among four quadrants, the upper right quadrant 102, upper left quadrant 104, lower left quadrant 106 and lower right quadrant 108, as divided by the median axis 110 and transverse axis 112. The lower edge of the ribcage is illustrated by the dotted line 114 and the diaphragm is shown at 116. The diaphragm 116 is shaped like a parachute and sits within the ribs. The esophagus 118 passes through the diaphragm 116 and joins with the stomach 120. The left lobe 122 of the liver 121 lies anteriorly of the esophagus 118 and the fundus-cardia junction 119 and Angle of His 119A. In one aspect of the invention, a fillable device is implanted in an extra-gastric location (i.e., outside of the stomach) generally indicated at 124, and then filled to occupy a volume that the fundus 120f of the stomach would ordinarily expand into when the stomach is filled with food. An inferior, smaller portion of the device may occupy a lesser volume that the body 120b would ordinarily expand into when filled with food. The filled device prevents this expansion by the fundus, thereby limiting the volume of the cavity in the stomach to a much smaller volume than if the fundus had been allowed to expand into the space. Alternatively, the device is filled to apply pressure to the fundus of the stomach in a downward direction (e.g., in a direction toward the transverse axis 112 shown, with some transverse movement toward the median axis 110 shown), and optionally, additionally to the main body of the stomach, to reduce the volume inside the stomach to effect satiety in the patient with relatively less food ingested, relative to what the patient would require for satiety without the implant in place.

Devices

Volume-reducing devices are described herein that are configured to be implanted in the abdominal cavity, externally of the stomach to fill a volume in the abdominal cavity that the stomach would otherwise occupy or be expandable into to occupy. Such devices permit movement of the stomach with respect thereto, but are anchored to at least one internal abdominal structure to prevent migration of the device from its intended volume-reducing location and/or orientation. Devices having various configurations of fillable members are provided, where a device can contain one or more fillable members and one or more steps of implantation and anchoring may be performed laparoscopically with remaining steps being performed percutaneously. Further alternatively, implantation and anchoring of a device may be performed with most if not all steps being performed laparoscopically or orally through a trans-gastric procedure. Any of the devices described herein can, of course, be implanted using open surgical procedures. Devices that can be implanted percutaneously can alternatively be implanted using laparoscopic procedures.

Devices described herein can be implanted permanently, but are also configured for reversibility, to facilitate relatively simple removal procedures, should it be desired to remove a device. Alternatively, devices according to the present invention can be implanted temporarily, such as over a period of months, and then removed or disabled when further treatment is no longer required, or to allow an alternative treatment to be applied.

Figure 2:
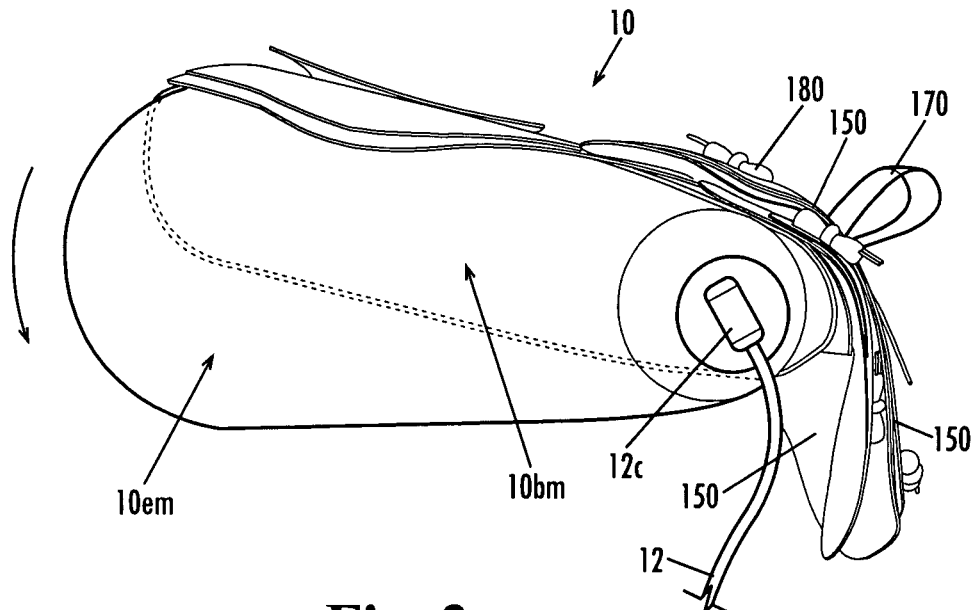
FIG. 2 illustrates an embodiment of a device that includes a buoyancy member within a fillable member according to the present invention.

FIG. 2 illustrates an embodiment of device 10 that includes a buoyancy member 10bm within fillable member 10em where buoyancy member 10bm is formed in the shape of an elongated spine. In this particular embodiment, buoyancy member 10bm is an elongated member having a curvature that generally corresponds to the curvature of fillable member 10em in the filled configuration, to follow the contour thereof. Alternatively, buoyancy member 10bm could be formed as a straight tubular member. In either configuration, the length dimension of buoyancy member is such to extend over at least half the length of fillable member 10em or at least two thirds of the length of fillable member 10em or at least three quarters of the length of fillable member 10em. In either the straight or the curved configuration, the length of buoyancy member distributes the buoyancy more equally over the volume of the filled fillable member 10em, compared to a buoyancy member 10*bm* that is allowed to float to one particular location of a fillable member. The embodiment having a curvature that somewhat conforms to the curvature of the filled fillable member 10*em* has been found to distribute the buoyant forces even better than a buoyancy member having a straight configuration. This distribution of the buoyancy forces helps to maintain the filled fillable member 10*em* in the desired location, as well as orientation that it is implanted in, as it minimizes any torquing forces or other uneven forces that a less well distributed buoyancy member may place on the filled fillable member. In this embodiment, like all other embodiments described herein, buoyancy member 10*bm* can be sized to provide an amount of buoyancy that, when combined with filled fillable member 10*em*, provides a substantially neutral buoyancy when implanted outside of the stomach in the abdominal cavity of the patient. Neutral buoyancy refers to device 10 having a density about the same as the density of the surrounding environment outside of the stomach in the abdominal cavity in which the device is implanted. Accordingly, device 10 will thus not tend to either sink or float in the abdominal cavity, but have a tendency to remain substantially in the location implanted.

The environment outside the stomach in the abdominal cavity in which the device is implanted can be considered fluid in the sense that, if a balloon that is completely air-filled is placed therein, the balloon will tend to float to the highest location in fluid environment of the abdominal cavity, and such location will vary, depending upon the orientation of the patient. Thus, the balloon will tend to migrate about as the patient lies down, rolls over while lying down, stands, etc. For these reasons, buoyancy members are provided herein with a density less than a density of the fillable member when the fillable member is filled with liquid, so that, in combination with the fillable member, the combined density of the device substantially matches the density of the environment outside of the stomach in the abdominal cavity. In this way, the device will not tend to attempt to "float" or pull away from an anchored/implanted location, and, in situations wherein at least a portion of the device is not directly fixed, will prevent unwanted migrations of these portions. This same concept could be applied to an air or other gas-filled fillable member, but where the buoyancy member would have a density greater than the density of the fillable member when the fillable member is filled with gas.

The density of the environment outside of the stomach in the abdominal cavity is typically about 900 to about 1100 kg/m$^3$ depending upon the amount of fat present in the abdominal cavity, sizes of the organs, fill state of the stomach, and other factors. This estimated range was calculated from some of the densities of structures within the abdominal cavity, where fat has a density of about 916 kg/m3, the stomach has a density of about 1048 to about 1050 kg/m$^3$ and the liver has a density of about 1050 to about 1070 kg/m$^3$, for example. The devices described herein can be designed to have a combined density in that range to be substantially neutrally buoyant. For example, if the fillable member 10*em* is filled with saline, having a density of about 1009 kg/m$^3$, then the buoyancy member 10*bm* will need to have a density substantially lower than 1009 kg/m$^3$, and corresponding volume to lower the density of the device 10 to a range of about 916 kg/m$^3$ for a patient that has a substantially fat-filled abdomen. Neutral buoyancy describes the scenario where an object is submerged in a fluid and tends to neither sink downward nor rise upwards.

Alternatively, this embodiment, or any other embodiment described herein, may be configured to have slightly positive buoyancy. This slight (e.g., less than 0.2 pounds positive buoyancy when implanted, typically much less than 0.2 pounds but greater than zero pounds) buoyancy tends to right the device in a situation where the positive buoyancy is applied in a superior portion of the fillable member and the patient is in an upright sitting or standing position, for example. An alternative technique for adding buoyancy, such as to adjust a displaced device, or that can even be utilized at the original implantation of the device, is to input a small quantity of gas into the liquid filled fillable member 10*em*. This can be done at the time that the fillable member 10*em* is filled with liquid, or, for example, on a subsequent patient visit. When done subsequently, the physician may optionally withdraw a small amount of liquid to provide space to be occupied by the small gas volume.

Accordingly, depending on the relative volumes and densities of fillable member 10*em* and buoyancy member 10*bm*, device 10 can: 1) reduce the overall density to reduce the relative "weight" of the implant within the abdomen (i.e., a neutrally buoyant implant will neither sink nor float but maintain a relatively stable position relative to the surroundings in the abdominal cavity); 2) achieve neutral buoyancy within the abdomen; or 3) achieve a slightly positive buoyancy that helps orient the device 10 upwards into a desired position and orientation (e.g., located against the fundus and the diaphragm).

In one particular embodiment, the buoyancy member 10*bm* of FIG. 2 is a porous polymeric foam or sponge member with an outer layer or cover, such as silicone, for example, designed to provide a predetermined amount of positive buoyancy for the particular volume of the fillable member 10*em* that it is installed in, such that when fillable member 10*em* is filled with liquid to its filled volume, the device 10 exhibits relatively neutral or slightly positive buoyancy in its implanted location outside of the stomach in the abdominal cavity, as described above. Thus, the combination of the positive buoyancy force provided by buoyancy member 10*bm* and the negative buoyancy force provided by the liquid-filled fillable member 10*em* combine to provide a substantially neutral (or very slightly positive) overall buoyancy force by device 10. Buoyancy member 10*bm* does not contain a central cavity to hold a gas therein, but is an expanded polymer structure, such as a foam or sponge, or other form of expanded polymer. In each case, the expanded polymer has a density that is less than the density of the same polymer in an unexpanded form. The expanded form includes pores as gas-containing features, but otherwise includes no hollow structures. Thus, the only gas-containing features are the pores formed in the expanded polymer structure. The buoyancy member may be formed as a closed-cell foam or an open-cell foam encapsulated by a non-porous polymer layer. Thus, the buoyancy member is molded as a "solid" object, i.e., with no central cavity, and the only features that are gas-filled are the pores of the expanded polymer structure. The buoyancy member therefore exhibits substantially uniform density throughout the entirety thereof, with the exception of any skin layer that may be present, which is not porous. In one particular embodiment, the buoyancy member is made of silicone foam, which is described in more detail below. However, other polymers may be used, such as polyurethane, or the like, for example.

When, as shown in FIG. 2, buoyancy member 10*bm* is not allowed to free float, but is fixed in some manner relative to fillable member 10*em*, this may reduce the risk of failure due to wear that might possibly be caused by repetitive contact between buoyancy member 10*bm* and fillable member 10*em* when buoyancy member 10*bm* is allowed to free float.

In the example shown in FIG. 2, buoyancy member 10bm is not fillable, inflatable or expandable, but is formed as a substantially solid member, as noted, with only pores of the foam or sponge containing gas. Buoyancy member 10bm is thus somewhat rigid and provides structural support to the fillable member 10em, functioning like a "backbone" of device 10, in addition to providing the positive buoyancy force described above. Buoyancy member 10bm can be described as having a curved, substantially cylindrical shape or "stomach-mimicking" shape, that mimics the shape of the fillable member 10em of FIG. 2, but is smaller in size than the size of the fillable member 10em. The outside diameter of buoyancy member 10bm is kept relatively small to facilitate insertion of device 10 (described in more detail below) trough a minimally invasive opening in the patient. Thus, for example, the maximum outside diameter of buoyancy member 10bm is typically no greater than about 2.00", or no greater than about 1.85", or no greater than about 1.5", typically, about 1.60" to about 1.85". In this way, fillable member 10em can be compressed down around the buoyancy member 10b for delivery through a small opening in a patient.

Buoyancy member 10bm in FIG. 2 forms an internal spine in fillable member 10em and distributes the buoyancy forces by being shaped proportionally to the filled shape of fillable member 10em. For example, in FIG. 2, fillable member is substantially stomach-shaped when in the filled configuration shown. Likewise, buoyancy member 10bm is also substantially stomach-shaped, and is fixed to fillable member 10em to generally follow the contours of the fillable member 10em in the filled configuration. This arrangement substantially distributes the buoyancy forces in a weighted distribution pattern that matches the weight distribution of the liquid in the fillable member 10em when it is filled. Accordingly, the buoyancy forces are distributed as stably as possible, to minimize any torquing or other uneven forces that buoyancy member 10bm might otherwise apply to device 10 when implanted.

Buoyancy member 10bm is typically fixed to fillable member 10em along the entire length of buoyancy member 10bm. In the example shown, buoyancy member 10bm is fixed to an internal surface of fillable member 10em. Buoyancy member 10bm has a maximum outside dimension (e.g., outside diameter, or other cross-sectional dimension) that permits it, together with device compressed down around it, to be inserted through a small incision in a patient. Examples of such maximum outside dimension are those described above.

Buoyancy member 10bm may be formed with a twist along its longitudinal axis, so that the external surface of buoyancy member 10bm that is fixed to the fillable member 10em follows a curvature resulting from the twist that is determined to better follow the contour of the inner surface of fillable member 10em. It is further noted that the wall of fillable member 10em can be reinforced in the location where buoyancy member 10bm is attached thereto, as described in greater detail below. Buoyancy member 10bm may additionally be curved in a second dimension relative to the dimension of the curvature described above. Such a complex curvature may best fit the complex curvature of the inner surface of fillable member 10em where buoyancy member 10bm is attached. Such a complex curvature allows the spine/buoyancy member 10bm to start and end at the most desirable locations to structurally support the fillable member 10em. For example, in this embodiment, the start point is among the attachment tabs 150 (e.g., see FIG. 2). The structure of the spine 10bm then extends from the abdominal attachment location of the fillable member 10em to the furthest apex of fillable member 10em and thus performs two functions: 1) spine/buoyancy member 10bm provides structure which helps to transfer the weight of the cantilevered fillable member 10em (when anchored to the abdominal wall via attachment tabs 150, the device 10 extending from the attachment tabs 150 into the abdominal cavity forms a cantilever structure) back to the abdominal attachment; and 2) spine/buoyancy member 10bm provides the most buoyancy at the apex portion/superior portion of fillable member 10em, so as to minimize twisting forces and lifting on inferiorly located portions.

By resisting bending forces that may be induced on this cantilever structure (e.g., see arrow in FIG. 2), buoyancy member 10bm functions as a spine and prevents creasing/wrinkling of fillable member 10bm, thereby greatly increasing longevity of the fillable member, as repeated cycling of crease formations can cause wear (abrasion) and eventual failure of a fillable polymer film, such as a silicone fillable member, as has been determined in breast implant cases.

Figure 3A:
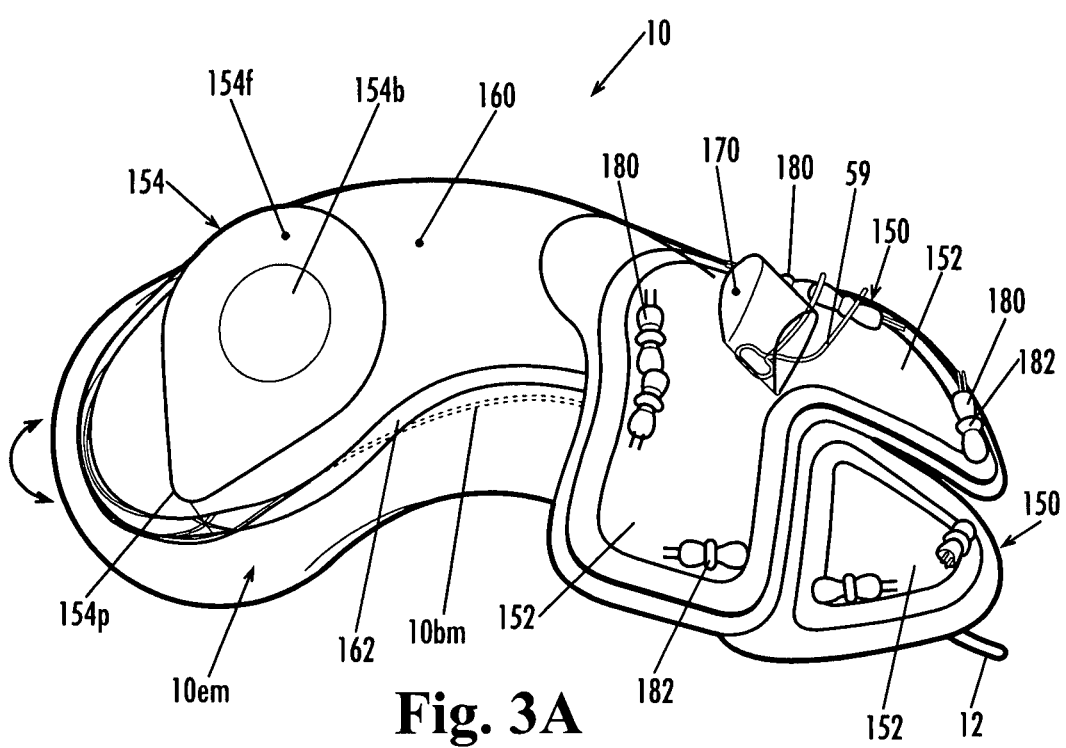
FIG. 3A shows an anterior perspective view (taken from the medial side) of an embodiment of a device having a buoyancy member attached to an inner wall surface of a fillable member thereof.

FIG. 3A shows an anterior perspective view (taken from the medial side) of an embodiment of device 10 having buoyancy member 10bm attached to an inner wall surface of fillable member 10em to form an internal, buoyant spine in a manner as described above. Fillable member 10em further includes at least one reinforcement layer 160 that extends over a majority of the length of fillable member 10em and may extend over substantially the full length of fillable member 10em. The portion of the wall of fillable member 10em covered by reinforcement layer(s) 160 typically includes at least the area opposite the area the buoyancy member 10bm is attached to, and may include a substantial margin beyond this area in any direction, up to and including all directions. Thus, buoyancy member 10bm is bonded to fillable member 10em only in locations that are further reinforced by reinforcement layer(s) 160. This prevents contact between buoyancy member 10bm and fillable member 10em in locations that are not bonded together, thereby preventing abrasion, erosion and wear, since the reinforcement layer(s) 160 prevent kinking of the fillable member layer in locations around the buoyancy member 10bm. Reinforcement layer 160, provides additional structural support of fillable member 10em to reduce chances of the filled configuration kinking by bending along its longitudinal axis. Cyclic actions of such kinking can produce wear and even failure of the fillable member, as noted, so the addition of reinforcement layer 160 performs a useful stiffening function. Together with buoyancy member 10bm functioning as an internal spine, this arrangement of reinforcement layer 160 and buoyancy member 10bm provides even more structural support to prevent kinking and otherwise maintain fillable member 10em in its desired orientation in the filled configuration. By providing the bond between the buoyancy member 10bm and fillable member 10em substantially along the interior surface of the anterior portion of the fillable member wall, this maintains the buoyancy forces provided by buoyancy member 10bm near the top of the device 10 when a patient is lying on his/her back, and this helps to maintain proper orientation of the device 10 as implanted. Also, since the superior end portion is positioned more posteriorly than the inferior end portion (when tabs 150 are fixed to the anterior abdominal wall), this orientation of buoyancy member 10bm also assists in properly orienting device 10 when the patient is standing or sitting, with application of buoyancy forces being able to be applied directly to the wall of the fillable member 10em without intervening expansion liquid, as this is substantially below and on the sides of the buoyancy member 10bm when so oriented.

Reinforcement layer 160 may be made, for example, of silicone sheeting reinforced with a strengthening material such as woven polyester, polytetrafluoroethylene, or the like. A margin 162 of unreinforced silicone can be maintained all around the edges of the sheet to facilitate bonding to fillable member 10em and to avoid stress concentration at the edges. Bonding can be performed, for example, using room temperature vulcanizing silicone adhesive, or vulcanizing a sheet or cut form of unvulcanized rubber, for example. Alternatively, reinforcement layer 160 may be made from a different polymer, such as polyurethane, for example, and reinforced with polyester mesh, for bonding onto a fillable member 10em having a polyurethane outer wall surface.

Alternative formulations from which fillable member 10em may be made include, but are not limited to: polyurethane compositions including silicone-containing chain extenders, such as taught in U.S. Pat. Nos. 6,420,452 and 6,437,073, for example, or segmented block polyurethane copolymers, such as taught in U.S. Pat. No. 5,428,123, or other combined polymer compositions of polyurethane and silicone resulting in less permeability (to gas and/or liquid) than that of polyurethane used alone, or silicone used alone. Additionally, these improved barrier (resistance to permeation) properties can be achieved with a thinner wall thickness than would be required if using polyurethane alone, or silicone alone. Optionally, buoyancy member 10bm may also be made from any of these same materials. U.S. Pat. Nos. 6,420,452; 6,437,073; and 5,428,123 are hereby incorporated herein, in their entireties, by reference thereto.

To facilitate anchoring of device 10, device 10 may be provided with one or more attachment tabs 150. Attachment tab(s) 150 fan out like wings from the surface of fillable member 10em to provide a much broader attachment surface area compared to what would be provided by simply attaching the portion of the fillable member 10em, from which they extend, to a structure. Tabs 150 are provided to extend radially outwardly in substantially all directions (relative to a two-dimensional plane) from the inferior end portion of the fillable member 10em to provide enhanced resistance to torquing and bending forces on the superior end portion of device 10. As shown, the resulting tissue ingrowth enhancing surface pattern formed by tabs 150 is substantially circular. This broader base of attachment is particularly useful in resisting bend movements in a plane perpendicular to that discussed above, for example, in the directions indicated by the bi-directional arrow in FIG. 3A. FIG. 3A illustrates a single lateral-medial attachment tab 150, wherein the right lobe of this tab extends laterally of the fillable member 10em and the left lobe extends medially of the fillable member 10em. A "tail tab" 150 is positioned inferiorly of lateral-medial tab 150 and extends inferiorly of the inferior end of fillable member 10em. Attachment tabs 150 may be bonded to the surface of fillable 10em, such as with silicone dip layer, for example, or using room temperature vulcanizing silicone adhesive, or using unvulcanized silicone sheeting between tab(s) 150 and fillable member 10em and then vulcanizing by heat pressing. By bonding to a portion of reinforcement layer 160, stress forces generated by movements of the patient, for example, through attachment tab(s) which are anchored to the patient, can be distributed over the reinforcement layer 160. Additionally, border portions of tab(s) 150 can be sandwiched between fillable member 10em and reinforcement layer 160, thereby further reinforcing the connection between attachment tab(s) 150 and fillable member 10em. If the attachment tab(s) 150 is/are made from polyurethane to be bonded to a polyurethane fillable member 10em wall, a solvent bond can be performed using a slurry mixture of polyurethane. By extending the superior edge of tab 150 continuously and integrally across the width of fillable member 10bm, this strengthens the bond and eliminates stress concentrations that could lead to delamination of tabs individually bonded to opposite side portions of fillable member 10em.

By integrating the lateral and medial tabs 150 as a single lateral-medial attachment tab as shown in FIG. 3A, this provides a broader area of bonding relative to the reinforcement layer 160/fillable member 10em thereby providing greater resistance to delamination from peel forces that may be applied thereto, particularly at the superior edge of the bond, when bending forces such as those illustrated in FIG. 2 are applied. By making the tail tab 150 separate from the lateral-medial tab 150, an advantage is provided in that the tabs are more easily able to conform to the structure that they are being attached to, particularly if there is some curvature or other surface shape other than planar in the structure. That is, tabs 150 can be overlapped to reduce the overall coverage of the structure to be attached to and this increases the convexity of the attachment surfaces formed by tabs 150, or tabs 150 can be otherwise changed in relative position to better match a surface shape to be conformed to, or spread apart to increase the concavity of the attachment surfaces formed by tabs 150, for example. The overlapping prevents folds or wrinkles that would otherwise occur with a single tab 150. The use of attachment tab(s) 150 also gives the surgeon the option to not use conduit 12 to perform an anchoring function. This allows an access member connecting to conduit 12 outside of the abdominal wall to be placed further away from the ribs, potentially offering the patient less discomfort, and also allows conduit 12 to be placed so that it is not under tension to perform an anchoring function, thereby lessening the mechanical requirements for conduit 12. Attachment tabs 150, although typically located to extend from the inferior portion of fillable member 10bm, need not be so located, but can be placed to extend from any locations on device 10 or fillable member 10em.

Tab 150 will typically be formed from a reinforced sheeting, such as polyester-reinforced silicone sheeting, polypropylene-reinforced silicone sheeting or polyethylene-reinforced polyurethane sheeting for example, or any other biocompatible fabric that can be sandwiched between two layers of biocompatible polymers or rubbers. One or more patches 152 of tissue ingrowth enhancing material, such as an expanded polytetrafluoroethylene, polytetrafluoroethylene, polyester, etc, in felt or velour configuration, or polypropylene mesh, for example, can be bonded onto the reinforced sheeting so that, when placed in contact with tissue, tissue is encouraged to grow into the patches. A positioning loop 170 may also be provided to extend through lateral medial tab 150, as illustrated in FIG. 3A.

Alternatively, patches 152 of ingrowth material may be formed of the same material as the tab 150 that it is bonded to, although patch 152 has porosity of a size and density known to encourage tissue ingrowth thereinto. Patches 152 are bonded to tabs 150 only around the perimeters of the patches so as not to fill or partially block the porosity of the main body of each patch. Thus for example, if tabs 150 are made of silicone, patches 152 may be made of porous silicone. Likewise, if tabs 150 are made of polyurethane, patches 152 can be made of porous polyurethane. Patches 152 may be provided as mesh fabric made from multifilament yarns by any suitable method including, but not limited to knitting, weaving, molding, etc. Patches may be made porous by molding without manufacture from monofilament yarns.

Further alternatively, patches 152 may be formed in the material of the attachment tabs 150 themselves. That is, the area defined by patch 152 on tab 150 can be made porous, using molding techniques, or by bonding insert patches into openings of the tabs 150. However, it is generally preferred that the back surface of the patch 152 (the surface facing away from the surface that will interface with the abdominal wall) be covered with a layer that substantially resists tissue ingrowth, to prevent adhesions to other tissues in the abdominal cavity that are not intended to be attached to tabs 150.

Positioning loop 170 is connected to fillable member 10em and/or reinforcing layer 160 through tab 150 and tissue ingrowth enhancing material 152 which further reinforce the connection of loop 170 to the fillable member 10em. Positioning loop 170 is typically a short lightweight loop of polymer, such as a ribbon and may be formed from polypropylene mesh ribbon or the like, having a length sufficient to extend through and externally of the abdominal wall when tabs 152 abut the internal surface of the abdominal wall, but not long enough to be drawn all the way out through the skin of the patient. A suture 59 can be placed through and secured to loop 170, wherein the suture has sufficient length to be drawn out through the skin of the patient. By pulling only the suture 59 through the skin, without drawing the broader ribbon 70 through the skin, this has been found to be advantageous to better maintain insufflation pressure (when used) during surgery in the abdominal cavity.

After inserting device 10 through an opening in the patient and into the abdominal cavity (positioning loop 170 is also inserted into the abdominal cavity), a surgeon can form an additional puncture through the patient at another location in the abdomen in line with a location on the abdominal wall where it is desired to anchor the inferior end portion of device 10 to the abdominal wall. This puncture can be very minimal and performed using a needle, needle that includes a hook, or other sharp, minimally invasive tool. Using the same tool or a different minimally invasive hook tool or graspers, suture 59 is captured and drawn out through the additional puncture, thereby also drawing the loop 170 through the abdominal wall, but not through the subcutaneous fat or the skin. By applying tension to suture 59 and/or loop 170, the inferior end portion of device 10 and particularly ingrowth patches 152 can be drawn up against the internal surface of the abdominal wall for anchoring there. Anchoring of the tab(s) 150 can be done prior to or after filling of fillable member 10em. In one typical example, fillable member 10em can be filled with gas or liquid prior to anchoring to facilitate proper positioning of device 10 prior to anchoring tab(s) 150. One practical approach is to fill fillable member 10em with gas to check for positioning, since filling with gas is faster and easier than filling with liquid. Once proper positioning is confirmed, fillable member 10em can then be quickly deflated, and anchoring of attachment tab(s) can then be performed. By performing anchoring of attachment tab(s) with fillable member 10em at least partially deflated, this provides more working space and/or better visibility to accomplish the anchoring. Loop 170 can be sutured externally of the abdominal wall or to the external surface of the abdominal wall using suture 59. After anchoring, fillable member 10em can then be filled with liquid.

Device 10 may be further provided with one or more grasper tabs which are also referred to as grasping tabs or positioning tabs. One or more such grasping tab features may be provided on device 10, such as on fillable member 10em (typically over an area reinforced by reinforcing layer(s) 160) to assist in positioning/repositioning the device 10 in the abdominal cavity. In FIG. 3A, device 10 includes a positioning tab 154 that lies substantially flush with the surface of fillable member 10em, over a location that is reinforced with reinforcing layer(s) 160. Positioning tab 154 may be reinforced, e.g. a silicone sheet reinforced with polyester mesh, or the like. Only the central portion of tab 154 (bonded portion 154b) is bonded to fillable member 10em with the borders 154f left unsecured. Accordingly, graspers or other instrument can grab a portion of the free perimeter 154f at the border of positioning tab 154 to apply forces therethrough to move the position or orientation of fillable member 10. One or more of such positioning tabs can be bonded at any locations on the fillable member 10em that a surgeon may find useful to apply leverage to position or orient the fillable member. Once a tab is grasped by a tool, the tool can be pulled, pushed or otherwise manipulated to move the position of the fillable member 10em.

In the position and orientation shown in FIG. 3A (i.e., on the superior end portion of fillable member 10em oriented to point toward the Angle of His), a portion of the flange 154f of positioning tab 154 is formed as an arrow, pointer, or other indicator 154p that points toward and is aligned with the Angle of His when device 10 is properly positioned and oriented in the abdominal cavity where it is to be implanted. Indicator 154p may optionally be made radiopaque to facilitate viewing by fluoroscopy, although viewing will typically be performed laparoscopically. Thus, the surgeon can grasp tab 154 with endoscopic graspers or other instrument and push on grasp tab 154 via the instrument to move device 10 into position so that indicator 154p is aligned with the Angle of His. Once aligned, this provides feedback to the surgeon that device 10 has been properly located and oriented.

Figure 3B:
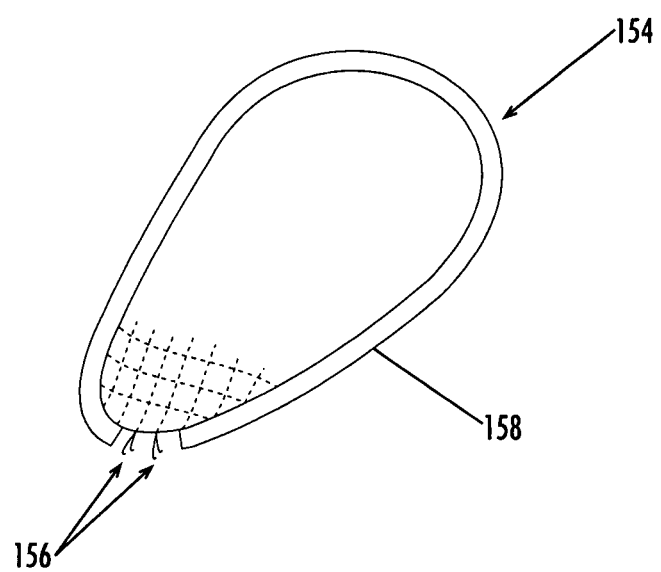
FIG. 3B illustrates frayed ends of cut reinforcing cable of a reinforcing mesh that can result in a positioning tab.

The reinforcing mesh that may be used in tabs 154, 150 and/or reinforcement layer(s) 160 may be formed of cables of the reinforcing polymer that forms the mesh. As such, when a die is used to cut through the tab/reinforcing layer and the reinforcing mesh, the cut ends of the cables may tend to unwind, or fray. FIG. 3B illustrates frayed ends of cut reinforcing cable 156 of a reinforcing mesh in positioning tab 154 that result when the shape of positioning tab 154 is die-cut from a sheet of polyester mesh reinforced silicone. In order to make a more atraumatic boundary and to ensure that the frayed ends 156 cannot contact the fillable member 10em and possibly cause abrasion, these frayed ends can be treated in a number of different ways to form an atraumatic boundary 158. One method involves applying a bead of RTV silicone over the frayed ends to produce a soft/atraumatic bumper 158 over the frayed ends. Another method involves die-cutting the tab or reinforcing layer to the shape desired and then inserting the tab or reinforcing layer into a mold designed to form the bumper 158 around the perimeter thereof. Silicone or other liquid polymer is then injected into the mold and cured to mold the bumper 158. Another method includes die-cutting the tab or reinforcing layer to the shape desired and heat forming a layer of unvulcanized silicone around the perimeter, where the heat forming vulcanizes the layer with the tab or reinforcing layer to produce bumper 158. According to a variation of the previously described method, unvulcanized silicone layers can be applied to both sides of the perimeter of the tab or reinforcing layer to sandwich the frayed ends, and then heat formed to vulcanize the three layers together and form bumper 158. Another method involves heating the die used to die cut the tab or reinforcing layer, to a temperature above the melting point of the polymer cables. The die is passed through the material of the tab or reinforcing layer slowly during the cutting process to afford enough time to melt the cable ends together, thereby preventing them from fraying. Alternatively, the die can be passed quickly to make the cut, and then reapplied to transfer the heat from the die to the cut ends of the cable to melt them and prevent fraying.

In one particular embodiment, device 10 is made almost entirely of silicone, with the exceptions of the tissue ingrowth enhancing patches 152, which are made of polyester velour, the polyester reinforcement of the reinforcement layer(s) 160, the polyester sutures 180 and 59, and the polypropylene mesh ribbon 170 (which also enhances tissue ingrowth of the fascia, externally of the abdominal wall). Accordingly, two different types of tissue ingrowth enhancing materials are used to increase the probability of tissue ingrowth. Conduit 12 is made of silicone and connector 12c that connects conduit 12 to fillable member 10em is also formed of silicone.

As noted, buoyancy member 10bm, is made of foam or sponge that encapsulates small gas pockets and therefore does not have to be filled after placement of device 10 in the abdominal cavity. Although shown as a curved cylindrical structure, buoyancy member 10bm can be any other shape that lends itself to being inserted through a small opening in a patient when fillable member 10em is compressed around it, although the curved cylindrical or curved stomach shape shown in FIGS. 2-3 is preferred for its efficiency in distributing buoyancy forces relative to the shape of fillable member 10em. A tubular or cylindrical shape particularly well lends itself to this task, as the device 10 takes on a somewhat cylindrical shape in the compressed state where a distal end portion can first be inserted through the opening of the patient with the rest of the cylindrical body being pushed through in a direction along the longitudinal axis of the cylindrical shape.

The foam used to make buoyancy member may be a silicone foam, or made from polyethylene or other biocompatible polymer for example. In each case, the foam is preferably a closed-cell foam having a skin, so that the cells of the foam are closed and encapsulate air or other biocompatible gas therein, to ensure that the buoyancy properties of the foam are maintained and the buoyancy member 10bm can therefore hold open a volume of gas and displace the liquid in fillable member 10em. However, in at least one embodiment of silicone foam buoyancy member 10bm described below, a very large portion of foaming agent is used in making the foam, and some of the closed cells burst and open to others of the cells, so the foam produced may not be entirely closed cell. This can also be the case when making a foam from another polymer when using a large portion of foaming agent. It should be noted that some manufacturers denote a "sponge" as a closed-cell material, and other denote a closed-cell material as a "foam". It should further be noted that, alternatively, an open-cell material may be used, when a layer of encapsulation is established around this open-cell sponge or foam. The encapsulation layer may be dip-molded onto the open-cell structure, or can be manufactured separately and then assembled around the open-cell structure. Such a configuration utilizes the open-cell foam or sponge to provide structural support to hold open the encapsulation layer. The encapsulation layer provides a barrier between the gas contained within the open-cell foam/sponge and the saline or other liquid contained in the fillable member 10em outside of the buoyancy member 10bm. An encapsulation layer may be provided over a closed-cell foam/sponge using any of the same techniques described above.

In one particular embodiment, the foam is a silicone foam made from silicone typically made to make a silicone sheet, but with a foaming agent (sodium bicarbonate) mixed with the silicone to make a slurry. For example, a silicone system known as MED-4840 by NuSil Technology, Carpinteria, Calif. may be used. The foaming agent used may be MED 4-4800, from the same company. The mixed slurry can be described as having a consistency like peanut butter and the slurry is packed into a mold and then heated at about 150° C. for about an eighty minute cycle, typically. For relatively larger molds, the heating cycle may be greater than eighty minutes to allow heat to penetrate and saturate the mold. The foaming agent, during the heat cycle, converts to water vapor, carbon dioxide and ammonia, thereby ensuring the biocompatibility of the resulting foam product. The mold is then removed from the heat and allowed to cool. After cooling, the foam product is removed from the mold and finished by removing any flash that may have formed. The finished product is a closed-cell foam that includes a skin layer both inside and outside. In another embodiment, the foam is polyethylene, which is expanded via high pressure carbon dioxide. The infusion of the carbon dioxide creates air pockets that form the foam, leaving a material that remains polyethylene which is therefore biocompatible.

The silicone foam buoyancy member is produced by mixing together two liquid silicone elastomer, MED 4840 precursors (foam parts "A" and "B") with a foaming agent (part "F") in a manner as noted above. Typically parts "A" and "B" are mixed in equal proportions, and the amount of part "F" is added so that it makes up from about 1% to about 50% of the slurry's weight or volume, with the remainder of the weight or volume being taken up by equal portions of parts A and B. When part F was added in an amount of about 1% to about 5% by weight of the total weight of the slurry, this produced a silicone foam or sponge product having a density of about 0.7 g/cc. By improving the molds and mold process used, the foaming agent portion F was able to be increased to an amount of about 30% to about 50% by weight, typically about 30% to about 40% by weight, of the total weight of the slurry, and this produced a silicone foam or sponge product having a density of about 0.39 g/cc to about 0.50 g/cc, typically about 0.44 g/cc. In one particular embodiment, the slurry is made up of about 35% by weight of foaming agent F (with parts A and B each making up about 32.5% by weight of the slurry) to produce a buoyancy member 10bm for use in a device to perform the functions described above and the foam produced thereby has a density of less than about 0.5 g/cc or less than about 0.045 g/cc.

Figure 4A:
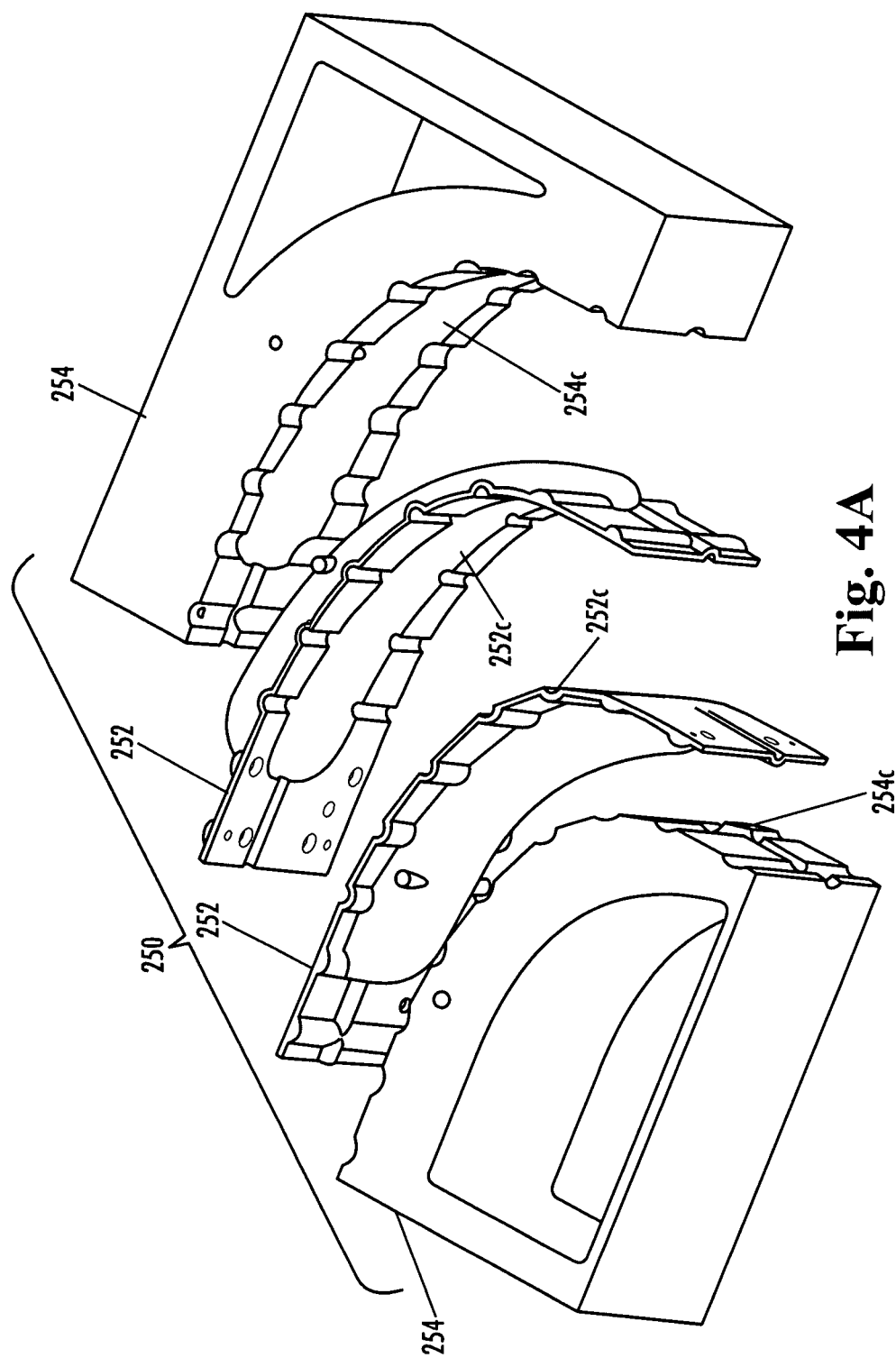
Figure 4C:
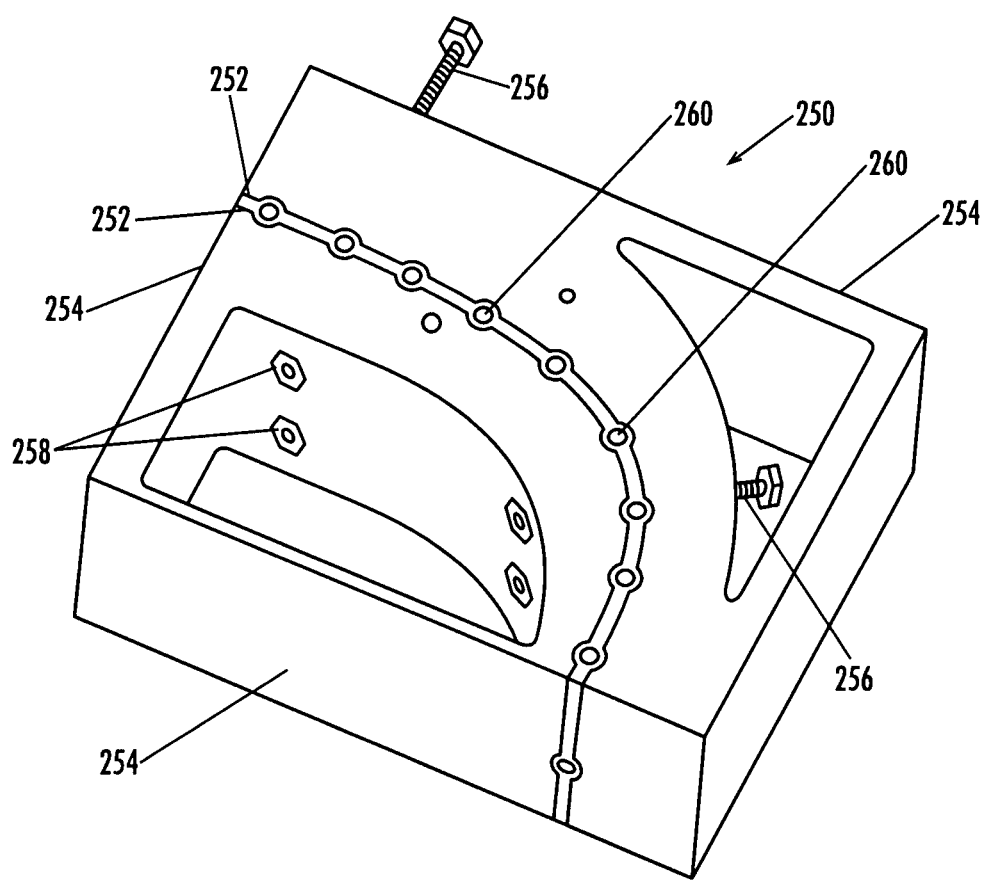

FIGS. 4A-4C show various views of a mold 250 used to form an expanded polymer product for use as a buoyancy member 10bm described herein. The mold 250 shown was specifically designed for forming the low-density silicone foam/sponge described above, but could be used to form the higher density silicon foam/sponge products or foam/sponge products made from other polymers. FIG. 4A shows an exploded view of mold 250 that includes non-stick insert portions 252 and support frame portions 254. Insert portions 252 may be made from polytetrafluoroethylene, for example, or other biocompatible high temperature polymer that can be used to form a non-stick surface, can withstand the molding temperatures, and will not contaminate the biocompatibility of the mold product (sponge/foam) formed. Inserts 252 can be produced by CNC (computer numerical control) machining to form the shape and dimensions of the product to be molded by the inner surfaces thereof when inserts 252 are joined together as illustrated in FIG. 4B.

Initially, it was attempted to make the entire mold 250 from polytetrafluoroethylene. However, the mold made entirely of polytetrafluoroethylene did not maintain sufficient rigidity at the elevated molding temperatures. Additionally, when the entire mold was made of polytetrafluoroethylene, its thermal insulation properties were too great, making it difficult to raise the temperature of the materials to be made into the foam in an acceptable time. As a result, inserts 252 are now thin-walled components and support frame portions 254 having cavities 254c that closely interfit with the external surfaces of inserts 252 to receive them therein are provided.

Support frame portions 254 are substantially thicker than inserts 252 and are metallic to provide excellent rigidity and thermal transfer during the molding process. In one embodiment, support frame portions 254 are aluminum, although other metals may be used including, but not limited to, steel, stainless steel, brass, etc. After completely filling the cavities 252c of inserts 252 with the slurry material having the peanut-butter-like consistency, the inserts 252 are joined together like shown in FIG. 4B and the support frame portions are joined together, like shown in FIG. 4C to close the mold 250. The mold components are held together under compression such as with bolts 256 and nuts 258, mechanical clamping, and/or some other form of mechanical compression, for example. Vents or gates 260 are provided to allow gases to escape from the materials as they are heated and/or to allow excessive materials to escape therefrom. This mold arrangement 250 allowed more foaming agent to be used than in previous embodiments and higher pressure and temperature to be generated during the molding process. The pressures generated were not measured, but the temperatures were increased from about 150° C. to about 175° C. to 200° C. Because the molds are largely aluminum and not all polymer this allows the processing temperature (and corresponding pressures) to be increased, as all polymer molds experience warping at these increased temperatures, but the present molds do not.

After the foam/sponge has been formed by the molding process, the mold is quenched and then air cooled before being opened. Alternatively, the mold can be allowed to cool down in the oven as the oven cools. After cooling, the mold is disassembled by removing the bolts, or other mechanical compression members and pulling apart the support frame portions 254. Inserts 252 are then separated and the molded product (foam/sponge) can be trimmed to remove any flashing or excess product that might extend from the intended boundaries of the foam/sponge. The foam/sponge is then dipped in silicone (in the case of a silicone foam/sponge product, other materials may be used to coat foams/sponges made from other polymers, or silicone could be used as well) to ensure a continuous, sealing coat of silicone over the entire external surface of the foam/sponge. More than one dipping step can be carried out to increase the thickness of the external polymer coating. Because the foam is silicone, the liquid silicone bonds very well to the foam to form the external coating, thereby making the coated product (encapsulated foam/sponge) liquid-proof, so that liquid in the fillable member 10em cannot enter the buoyancy member 10bm. This also improves the bond strength between buoyancy member 10bm and fillable member 10em as both components being bonded are smooth and continuous silicone.

Sizing

Device 10 sizes may vary depending on the size of the skeletal system of the patient into which device 10 is to be implanted, particularly the size of the rib cage. In this regard, one aspect of the present invention provides a kit of devices 10 of various sizes, wherein the fillable members 10em of the various sized devices can vary in length and/or volume (in a filled configuration) relative to the other devices in the kit. In one particular embodiment, four device 10 sizes are provided. In another embodiment, a fifth size is provided for patients with unusually large rib cages. However, it is noted that the present invention is not limited to only four different sizes of devices or five different sizes of devices, as more or fewer variations in sizes may be provided.

Figure 5A:
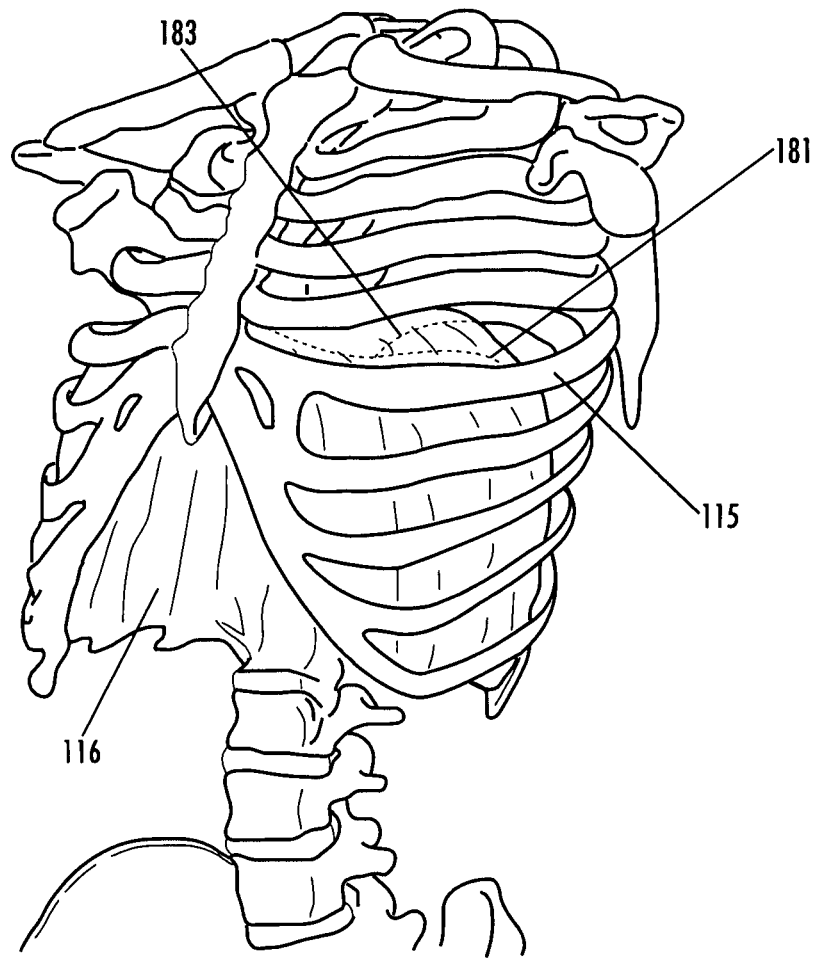
FIG. 5A illustrates Lateral and AP measurement lines used to take internal rib cage measurement of a patient.
Figure 5B:
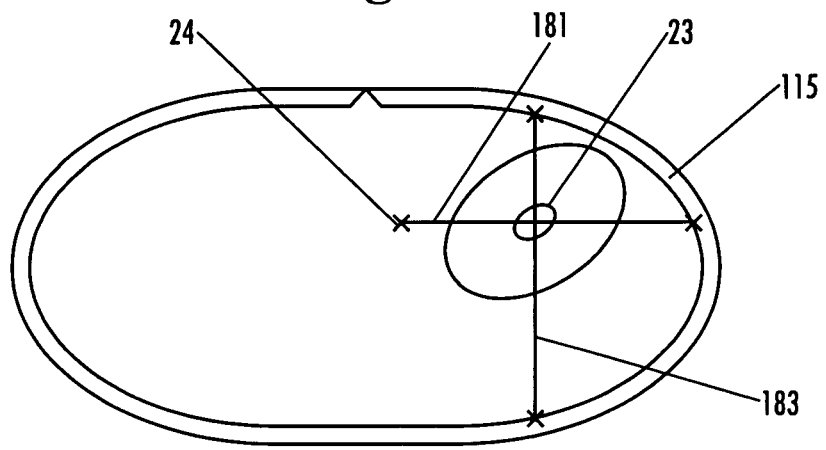
FIG. 5B illustrates an axial scan of an abdominal section of a patient, the slice being taken at the level of the gastroesophageal junction.

In order to select a particular device size that is optimal for a particular patient, the dimensions of the patient's rib cage can be measured. Referring now to FIGS. 5A and 5B, measurements are taken at internal points on the rib cage, at a level of the gastro-esophageal junction 23. A lateral measurement (Lateral) 181 is taken from midline 24 to the internal surface of the rib 115 at the level of the gastroesophageal junction 23, and an anterior-posterior (AP) measurement 183 is taken from the anterior-most point to the posterior-most point on the internal surface of the rib 115 at the level of the gastroesophageal junction taken through the center of the location of the gastroesophageal junction 23, along a line 183 perpendicular to the line 181 used to measure the Lateral measurement, as illustrated by the phantom lines in FIG. 5A. Typically these measurements are taken by CT/MRI scanning, although other known forms of three-dimensional imaging or two-dimensional imaging, such as X-ray, fluoroscopy or the like, may be substituted as would be readily apparent to those of ordinary skill in the art, upon reading this disclosure. Alternative measurement techniques include having the patient swallow a barium-containing solution and using a X-ray machine to perform measurement; measurement by ultrasound visualization, measure using PET scanning or CT scanning, measurement via laparoscopic visualization, etc. FIG. 5B illustrates an axial scan of an abdominal section of a patient, the slice being taken at the level of the gastroesophageal junction 23. From this scan, measurements of the lengths of lines 181 and 183 were made to provide the Lateral and AP dimensions, respectively. As noted above, the AP dimension 183 is measured from the posterior inside surface of rib 115 at the level of and through the center of the gastroesophageal junction 23 to the anterior inside surface of rib 115 at the level of the gastroesophageal junction 23. The Lateral dimension 181 is measured from midline 24 to the left lateral inside surface of rib 115, through the center of the location of the gastroesophageal junction 23 at the level of the gastroesophageal junction 23.

Depending upon the dimensions of the rib cage of a patient, the device 10 may need to be relatively longer or shorter and/or relatively larger or smaller in diameter (particularly at the more bulbous, superior portion) compared to the size of device 10 indicated for another patient with a different rib cage size, in order to accomplish the desired amount of volume occupation and maintenance of the stomach in a reduced configuration to the amount desired.

The AP and lateral measurements can be used to approximate the size of the fundus and body of the stomach 120 of the particular patient from which the measurements were taken. Using the AP and Lateral measurements as baseline measurements, scaled devices 10 can be produced to take up a desired amount of space that the stomach would otherwise be allowed to occupy and/or expand into. There is approximately a cosine relationship between the AP dimension and the length of device 10/fillable member 10bm, as what was observed is that the angle of the fillable member 10em as placed to approximate the stomach position is between about forty to about sixty degrees relative to the horizontal AP measurement. The relationship between the Lateral measurement and the largest diameter of the fillable member 10em is more linear, calculated to be a fixed percentage (e.g., about 40% to about 95%, or about 45% to about 90%, typically about 50% to about 90%. In at least one example, Target volumes were calculated to be about 70%, Mini volumes about 56% and Max volumes about 90%) of the Lateral measurement when fillable member is at the Target volume. The relationship between the Lateral measurement and the large diameter (i.e., diameter of the bulbous, superior portion) of fillable member 10em is more linear, where the large diameter is set to a predetermined percentage of the Lateral dimension measurement. These derived length and diameter dimensions provide the target fill volume of the fillable member 10em. The Mini fill volume of the devices is then calculated to be about fifty percent of the target fill volumes of the devices, respectively. Due to the expansive nature of the fillable member 10*bm*, it can be filled to the Mini volume where it has no wrinkles, further filled to the target volume, and still further filled to the Max volume.

Figure 6A:
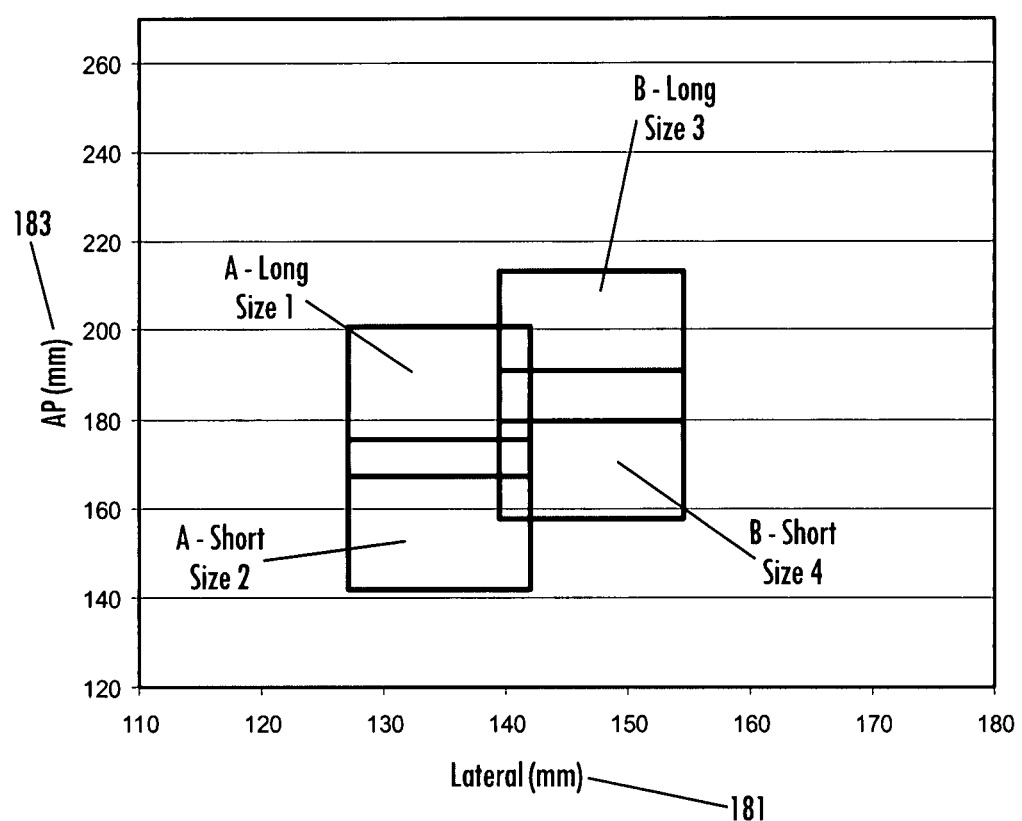
FIG. 6A illustrates a chart that correlates various sizes of devices with AP and Lateral rib measurements.
Figure 6B:
FIG. 6B shows another chart illustrating the ranges of AP and Lateral measurements covered by the various sized devices.

A chart has been devised to correlate the various sizes of the devices with the AP and Lateral measurements 183, 181 of the patient, so that a surgeon can readily select the appropriate size of device 10 to be used, see FIG. 6A. The expandability of the fillable members 10*em* allow them to be filled to an even greater volume than Max, for safety reasons. Although the fillable members 10*em* can even safely be filled to volumes greater than Max volume, this is typically not practiced. Each fillable member 10*em* is to provide as much of a useable volume range as possible. The Target volume is generally in the lower left corner regions of the boxes shown in FIG. 6A. The Mini volumes are designed so that the fillable members are generally ineffective, in case they need to be adjusted to this volume for emergency, pregnancy, accident, etc., and so the Mini volumes are outside of the boxes in FIG. 6A, further below and to the left of each lower left corner, respectively. The Max volume is represented upwards and to the right of the upper right corners of the boxes FIG. 6B shows another chart illustrating the ranges of AP 183 and Lateral 181 measurements covered by the various sized of implants. Either or both of these charts can be used to facilitate selection of an appropriately sized device for a patient, depending upon the AP and Lateral dimensions of that particular patient. These correlations, and the sizes of the devices have been designed so that fillable member 10*em* can be filled to compress the stomach 120 so that the internal dimension of the stomach is about 30 to about 34 French, typically about 32 French. It can be seen in FIG. 6A that there is some overlap of the applicable sizes for some chest measurements. In such cases, it is generally recommended to select the smaller (or smallest) device size 10 that is indicated.

Figure 7:
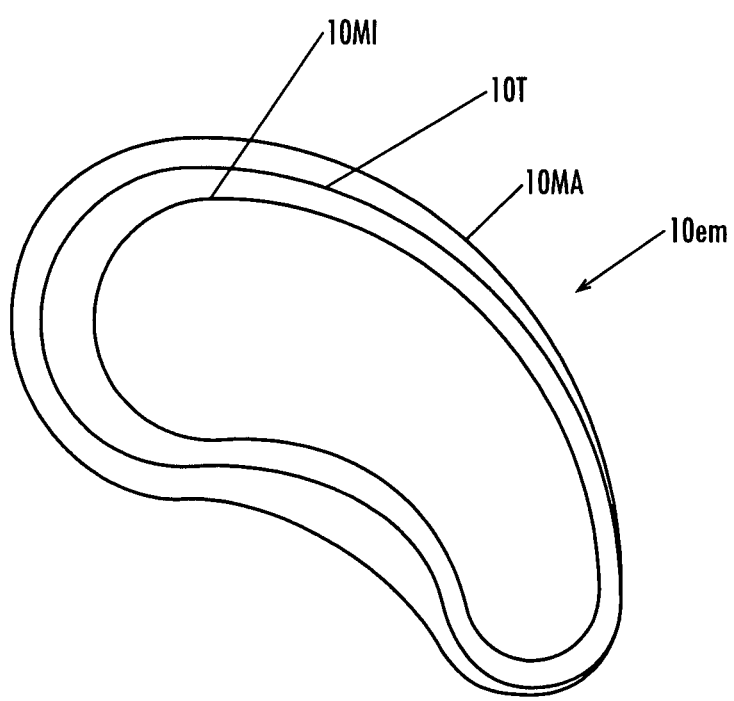
FIG. 7 illustrates the variation in lengths and diameters of fillable member 10*em* at the mini volume 10MI, target volume 10T and max volume 10MA.

The fillable member 10*em* of device 10 is designed to have a target volume 10T that it fills to in order to occupy a predetermined volume in the abdominal cavity to maintain the stomach 120 is a reduced configuration, as described above. Because these devices are designed to cover a range of sizes of rib cages, and in order to address other issues (e.g., the patient may be uncomfortable with a device 10 having been implanted and filled to the target volume 10T) Each fillable member 10*em* is designed to be fillable to a "Mini" volume 10MI where the fillable member 10*em* is filled to an extent where no wrinkles exist in the material of the wall of the fillable member 10*em*. Typically, the material of the wall of fillable member will not be elastically deformed, or only minimally elastically deformed in the mini volume configuration. When filled to the mini volume 10MI, the fillable member typically has about half the volume (e.g., about fifty to sixty percent of the target volume) that is has in the target volume 10T configuration, but the walls of the fillable member are under sufficient pressure so that there are no wrinkles in the walls. By configuring fillable member 10*em* to be reduced to the mini configuration 10MI, this gives the surgeon considerable leeway to adjust the volume of the fillable member 10*em* downwardly, while still maintaining the fillable member 10*em* in a configuration which substantially prevents bending, creasing and/or erosion of the materials forming the wall of the fillable member 10*em*. Additionally, in order to provide the surgeon with the ability to adjust the volume displacement of device 10 upwardly from the target volume 10T configuration, fillable member is configured to be safely fillable to a maximum (Max) volume configuration 10MA which is at least about fifty percent larger than the target volume 10T. FIG. 7 illustrates the variation in lengths and diameters of fillable member 10*em* at the mini volume 10MI, target volume 10T and max volume 10MA. Buoyancy member 10*bm* is designed to provide substantially neutral buoyancy (or slightly positive, e.g., about 0.03 pounds) in the environment that it is implanted outside of the stomach in the abdominal cavity, when combined with the fillable member 10*em* filled with saline to the target volume 10T. Thus, when fillable member is at the mini volume 10MI, device 10 is slightly positively buoyant in the environment that it is implanted outside of the stomach in the abdominal cavity, and when fillable member 10*em* is at the max volume 10MA, device 10 is slightly negatively buoyant in the environment that it is implanted outside of the stomach in the abdominal cavity.

Thus, devices 10 are provided with fillable members 10*em* that have a sufficient range of fillability to ensure that device 10 functions as intended and prevents the stomach from expanding in a manner as desired. The ability to reduce the volume (particularly to volumes less than target 10T), this provides additional advantages in that the device can be substantially reduced in sized without jeopardizing the longevity of the fillable member 10*em* by allowing it to wrinkle. For example, if a patient becomes pregnant or has the flu or some other need for rendering the device 10 less effective, or for at least reducing the constraints provided by device 10, the surgeon can reduce the volume of the fillable member 10*em* to as low as the mini volume 10MI without allowing the fillable member 10*em* to wrinkle. If the problem with the patient is temporary (such as flu, pregnancy, etc.), the volume of fillable member can be increased back to its previous volume after the temporary problem has ended, thereby returning device 10 to its former effectiveness.

Figures 8A, 8B:
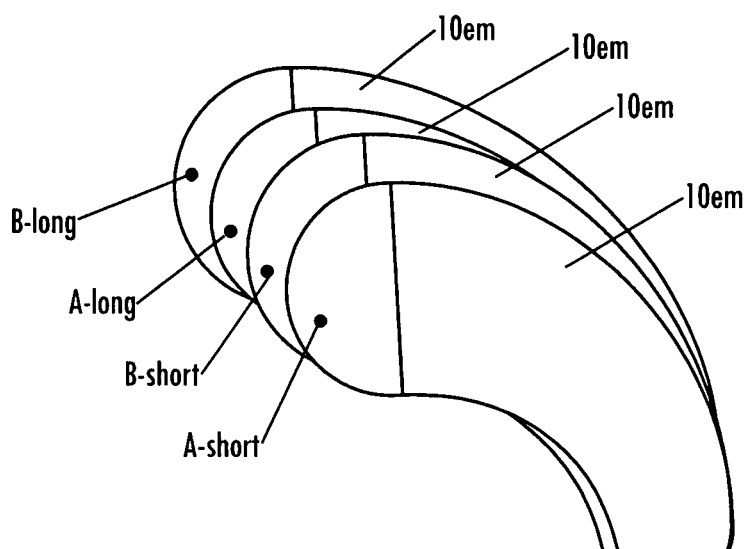
FIG. 8A is a chart that shows Mini, Target and Maximum volumes of an exemplary set of devices according to one embodiment having fillable members.
FIG. 8B visually compares the four fillable members referenced in FIG. 8A, the fillable members having been filled with saline to their Target volumes.
Figure 8C:
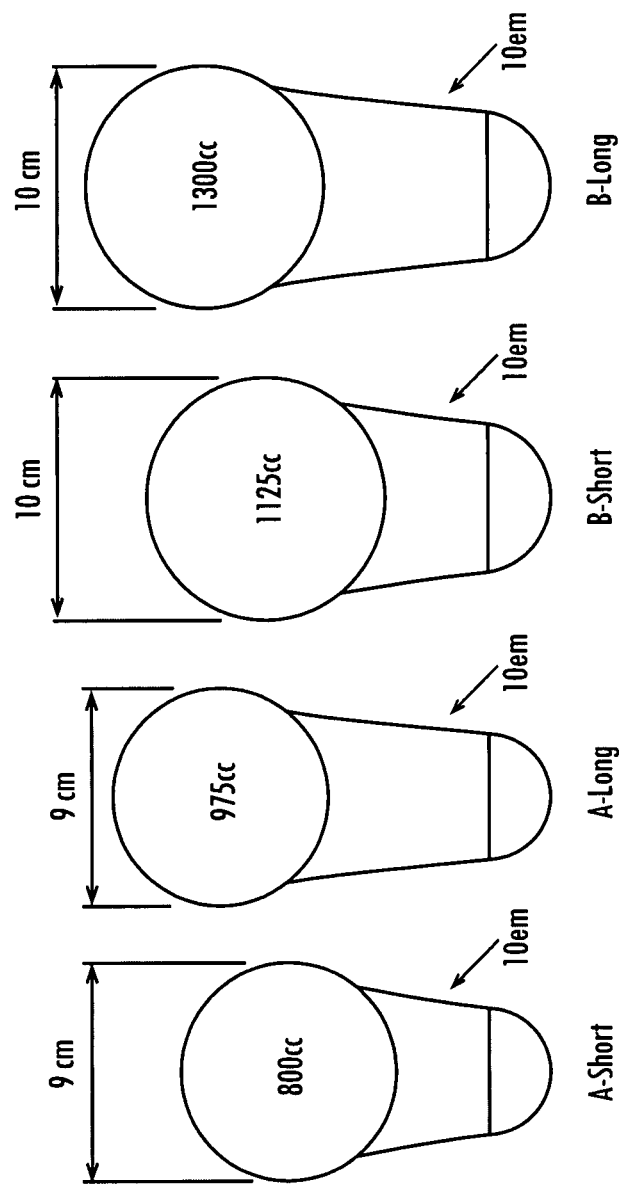
FIG. 8C illustrates differences in diameters of the somewhat bulbous, semi spherical superior end portions of fillable members of different sizes.

FIG. 8A is a chart that shows Mini 10MI, target 10T and Maximum 10MA volumes of an exemplary set of devices according to one embodiment having fillable members designated sizes, 1, 2, 3 and 4 (A-long, A-short, B-long and B-short), respectively. FIG. 8B visually compares the four fillable members having been filled with saline to their target volumes 10T and readily shows the differences in lengths among the four fillable members 10*em*. FIG. 8C illustrates the differences in diameter of the somewhat bulbous, semi spherical superior end portions of fillable members 10*em*. Due to the significant range in volumes achievable by each size it can be seen that there is significant overlap in volumes that are achievable by the fillable members of the various sizes 1-4. This can be advantageous if the size of device is incorrectly selected. Thus, for example, if a patient should have a size 4 device (B-short) with a target volume 10T of 1125 cc, but for some reason is implanted with a size 2 device (A-short), the size 2 device can be filled up to the 1125 cc volume and still perform satisfactorily, since the size 2 device has a max volume 10MA of 1200 cc.

Figure 8D:
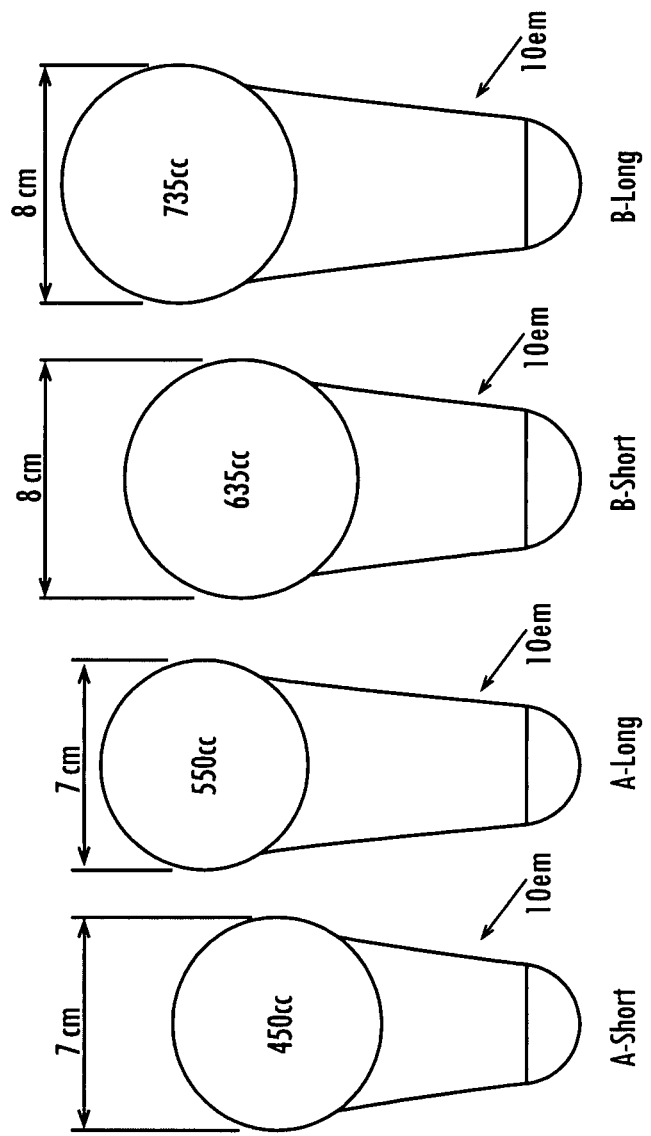
FIG. 8D illustrates the diameters of the superior end portions of the various sizes of fillable members of FIG. 8C when the fillable members are filled to the mini volume.

FIG. 8C shows that sizes A-short (size 2) and A-long (size 1) have the same diameter of the superior end portion of about 9 cm when filled to the target volume, but A-long has a greater length, so that target volume for A-long is about 975 cc, while the target volume for A-short is about 800 cc. Likewise, sizes B-short (size 4) and B-long (size 3) have the same diameter of the superior end portion of about 10 cm when filled to the target volume, but B-long has a greater length, so that the target volume for B-long is about 1300 cc, while the target volume for B-short is about 1125 cc. FIG. 8D illustrates the diameters of the superior end portions of the various sizes of fillable members 10*em* of FIG. 8C when the fillable members 10*em* are filled to the mini volume levels 10MI. As shown, the fillable members 10*em* are filled to an extent where no wrinkles exist in the walls of the fillable members 10*bm*, but the amount of expansion is significantly less than the target volumes, as can be seen by comparing the respective sizes of the fillable members between FIGS. 8B and 8D and by the volume numbers listed in FIG. 8A.

Figure 9A:
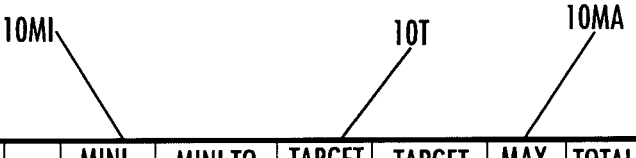
FIG. 9A is a chart that lists the increases in volume exhibited by the fillable members for sizes 2, 1, 4 and 3, respectively.
Figure 9B:
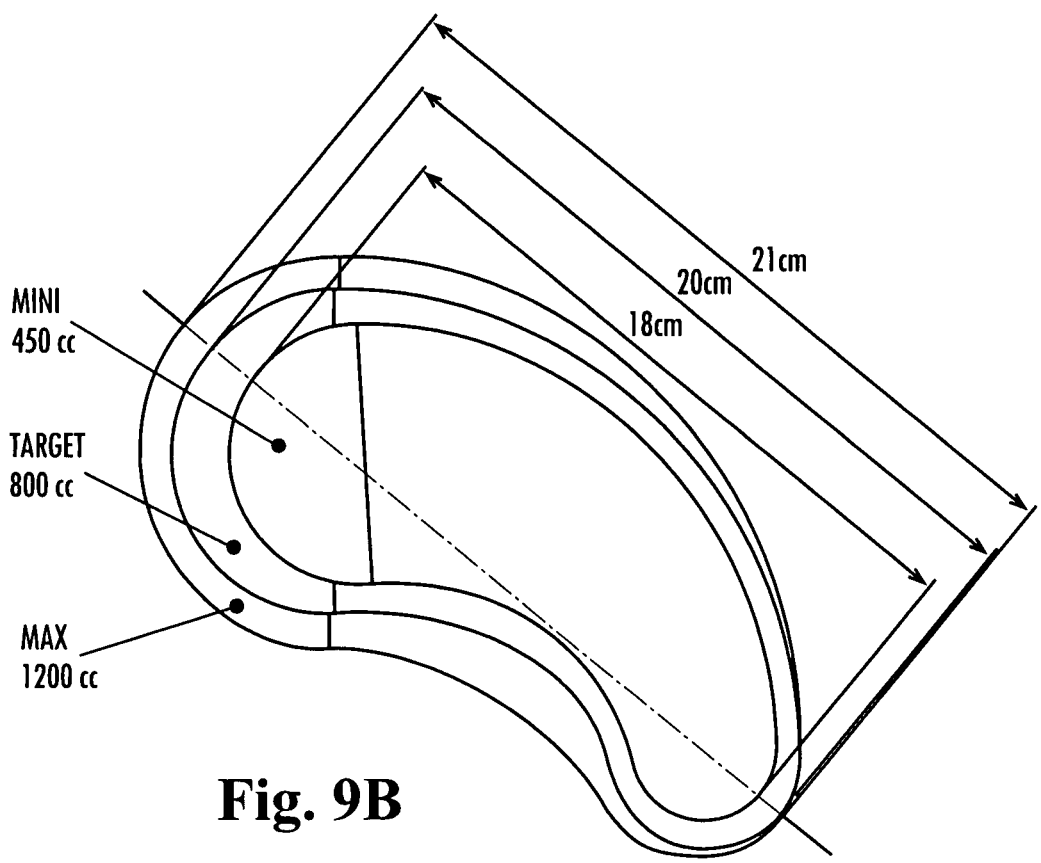
FIG. 9B illustrates the changes in the volume, length and shape exhibited by the fillable member for size 2.

FIG. 9A is a chart that lists the increases in volume exhibited by the fillable members 10*em* for sizes 2, 1, 4 and 3, respectively, when filling from mini volume 10MI to target volume 10T, when filling from target volume 10T to max volume 10MA, and overall volume increase from mini volume 10MI to max volume 10MA. FIG. 9B illustrates the changes in the volume, length and shape exhibited by the fillable member 10*em* for size 2 (A-short) wherein the fillable member has a length of about 18 cm at the mini volume fill configuration of about 450 cc of liquid, a length of about 20 cm at the target volume fill configuration of about 800 cc of liquid, and a length of about 21 cm at the max volume fill configuration of about 1200 cc of liquid. It can also be seen that the diameter of the fillable member increases as well as the length during filling from mini to target to max volumes, and examples of the size changes are shown in FIGS. 8C and 8D.

The shapes, lengths, diameters and volumes of sizes 1, 3 and 4 change similarly to that shown in FIG. 9B. For size 1 (A-long), the fillable member 10*em* has a length of about 22 cm at the mini volume filling level of about 550 cc of liquid, a length of about 24 cm at the target volume filling level of about 975 cc of liquid, and a length of about 26 cm at the max filling volume of about 1462 cc of liquid. For size 4 (B-short), the fillable member 10*em* has a length of about 20 cm at the mini volume filling level of about 635 cc of liquid, a length of about 22 cm at the target volume filling level of about 1125 cc of liquid, and a length of about 24 cm at the max filling volume of about 1687 cc of liquid. For size 3 (B-long), the fillable member 10*em* has a length of about 23 cm at the mini volume filling level of about 735 cc of liquid, a length of about 26 cm at the target volume filling level of about 1300 cc of liquid, and a length of about 28 cm at the max filling volume of about 1950 cc of liquid.

FIG. 10 is a chart that illustrates the relative volume of the buoyancy member 10*bm* and the liquid (in this case, saline) volume contained in the fillable members 10*em* at the various mini, target and max volumes, 10MI, 10T and 10MA, respectively. Note that since the buoyancy member 10*bm* in this case is a "solid" expanded polymer member, it is not fillable or fillable and thus occupies the same volume whether fillable member is at the mini volume 10MI, target volume 10T or max volume 10MA. For the A-short size 2, buoyancy member 10*bm* occupies about 181 cc volume; for the A-long size 1, buoyancy member 10*bm* occupies about 235 cc volume; for the B-short size 4, buoyancy member 10*bm* occupies about 243 cc volume; and for the B-long size 3, buoyancy member 10*bm* occupies about 292 cc volume.

According to at least one method embodiment of implanting a volume-occupying device 10 according to the present invention, an imaging apparatus is first used to measure the rib cage dimensions of the patient in the lateral direction and in the anterior-posterior direction. As noted above, these measurements are taken at about the level of the gastroesophageal junction and are measured from and to the opposite interior surfaces of the rib cage. Based on these measurements, a selection of an appropriate size of device 10 can be made for implantation into the patient. For example, the surgeon or other person doing the selection can refer to a chart, such as the chart shown in FIG. 6 for example, that shows a correspondence between the lateral and AP measurements and the size of device that is appropriate for a particular set of lateral and AP measurements. The appropriately sized device 10 can then be selected based on this established correspondence information. As noted, when the measurements are such that more than one size of device is indicated to be appropriate, the person will generally select the smaller (or smallest) appropriately-sized device.

Fillable members 10*em* may be formed to fill differentially along different portions of the wall of the fillable member 10*em*. For example, the surface of the bulbous superior portion that faces the stomach 120 when implanted may be formed to have a relatively thinner wall than the portion of the wall that is facing away from the stomach. Likewise, the portion shown in FIG. 9B that is concave may be thinner, so that it fills more prominently than the remainder of the fillable member when additional fluid is added. As another example, the wall of the smaller diameter inferior portion of fillable member 10*em* can be made significantly thicker than the wall of the bulbous superior portion, so the superior portion fills a greater amount than the inferior portion as fluid is added.

Figure 11A:
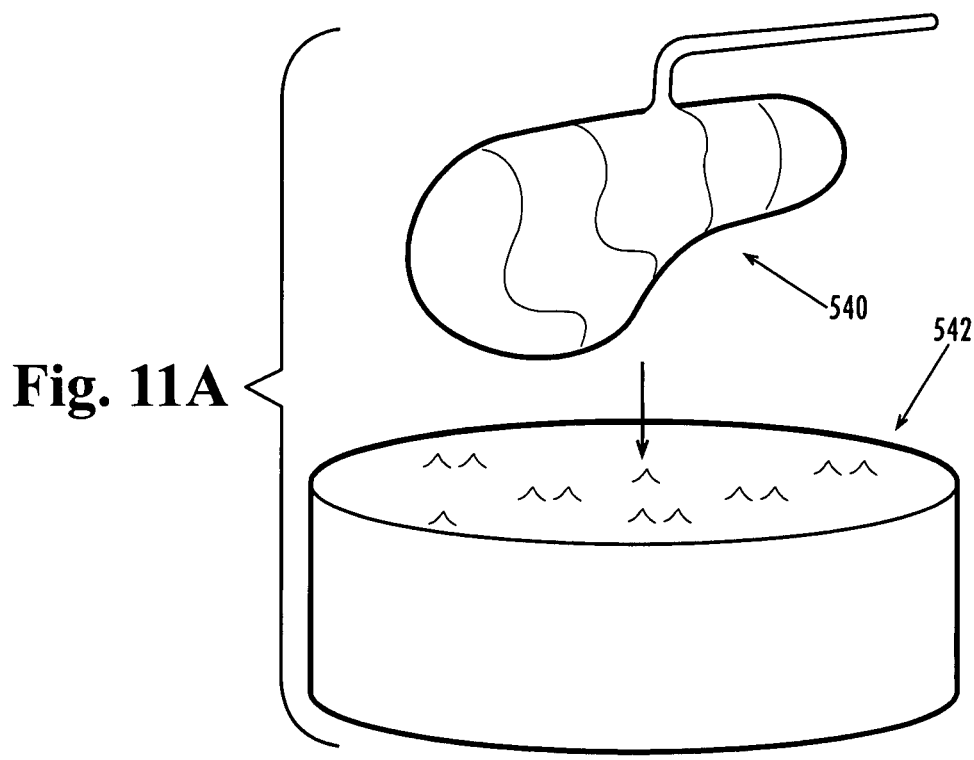
FIGS. 11A-11B illustrate an exemplary technique for making a fillable member that has varying wall thicknesses.
Figure 11B:
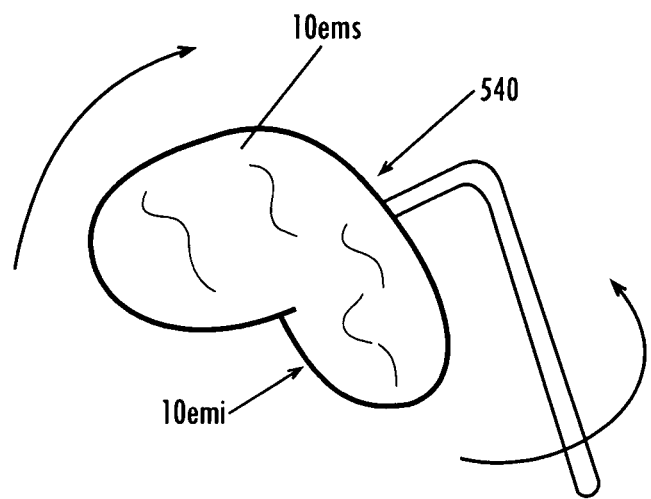

One exemplary technique for making a fillable member 10*em* that has varying wall thicknesses is illustrated in FIGS. 11A-11B. A mold 540 that has an outer surface conformation that matches the desired conformation of fillable member 10*em* is dipped into a vat 542 of liquid polymer (e.g., silicone, polyurethane or other biocompatible polymer or polymers) of the material that fillable member 10*em* is to be formed of, see FIG. 11A. After a predetermined time, mold 540 is pulled out of vat 540 and agitated, e.g., "twirled", rotated, or moved through a more complex pattern (such as by robotic control, for example) to distribute the polymer layer that has accumulated on the mold in a desired manner over the mold 540, while the polymer cures or solidifies, see FIG. 11B. Thus, for example, if it is desired to make the wall of the inferior portion 10*emi* thicker than the wall of the superior portion 10*ems*, then the movements can be performed, or programmed to be performed such that the inferior portion 10*emi* is at the bottom of the twirling cycle for a longer percentage of time than is the superior portion 10*ems*. With robotic control of this process, variations in thickness can be formed at any locations on the fillable member 10*em* that are desired. The steps in FIGS. 11A and 11B can be repeated until the various portions of the fillable member 10*em* have obtained the desired wall thicknesses. An alternative method is make the fillable member by a process of liquid injection molding. In this case, the mold into which the liquid is injected is formed to have the varying wall thicknesses desired.

In another method embodiment of implanting a volume-occupying device 10 according to the present invention, an imaging apparatus is first used to measure the rib cage dimensions of the patient in the lateral direction and in the anterior-posterior direction. As noted above, these measurements are taken at about the level of the gastroesophageal junction and are measured from and to the opposite interior surfaces of the rib cage. Based on these measurements, a device 10 having a size that is custom fitted to the particular measurements for the particular patient can be manufactured. Images of the abdominal cavity of the patient can be taken under both fasting and post-meal (where the patient has ingested as much as possible) conditions. The images can then be three-dimensionally reconstructed and used to tailor fit a device 10 to the imaged stomach sizes and/or Lateral and AP measurements. As noted, a custom device can be sized based only on the measurements taken of the stomach sizes, or can be sized based on the Lateral and AP measurements, or can be sized based on a combination of these. This custom fitting can account for variation in anatomy, such as different organ sizes and positions occupied during a post-meal condition, amounts of intra-abdominal fat present, etc.

For example, after the above-noted measurements and reconstructions are performed, measurements and/or specifications derived from the measurements and reconstructions can be sent to a manufacturing facility that manufactures a custom-designed device 10 for that particular patient. The dimensions and even the shape of device may be calculated from the AP and Lateral measurements and/or measured sizes and/or locations of the stomach under the fasting and post-meal conditions, either manually or by inputting the measurements into a computer programmed with an algorithm for calculating the dimensions and or shape of the fillable member 10em and buoyancy member 10bm, or dimensions and/or shape may be determined from one or more look-up charts that correlates one or more of the dimensions and shapes with AP and Lateral measurement values. Accordingly, rather than selecting a size 1, 2, 3, or 4 device 10, a device 10 is manufactured that may have one or more dimensions between and/or overlapping with the dimensions of the standard sizes 1-4. Although this takes some additional time until the patient can be operated on to implant device 10, this is not usually a critical consideration with the type of surgery being performed.

Figure 12A:
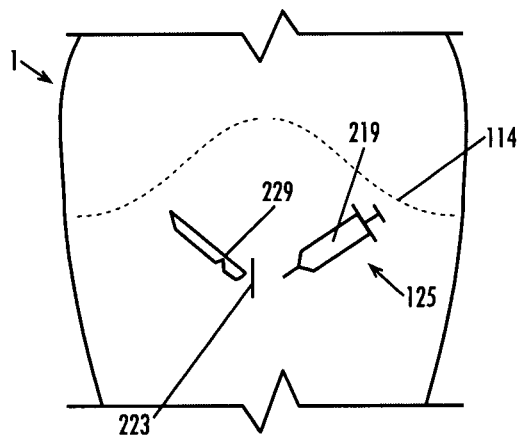
FIGS. 12A-12G illustrate steps and devices that may be used in an implantation procedure according to the present invention.

FIGS. 12A-12G are now referred to as an implantation procedure is described according to an embodiment of the present invention. Initially, an appropriately sized device 10 may be selected by taking Lateral and AP measurements of the patient's rib cage in a manner described above, and selecting an appropriate size of device 10 by referencing a chart like that shown in FIG. 6, or a custom-sized device 10 can be produced as described above. Once an appropriate device 10 is obtained and the patient 1 has been prepared for surgery, including disinfecting the local area (the area of the skin in and surrounding the location where the incisions are to be made), such as with alcohol and/or betadine, for example, the patient may be given a mild sedative or may be on conscious sedation. (Although not practiced in this particular procedure, a similar procedure could be practiced with placing the patient under general anesthesia, in which case anesthetics would not need to be injected as described in the next step.) Next a powerful local anesthetic such as marcaine (bupivicaine) or other powerful anesthetic, optionally mixed with an epinephrine or other vasoconstrictor to reduce any bleeding that might result from mild trauma, is injected into the local area through the skin 125 of the patient 1 down to the muscular layer and to infiltrate the fat layer and entire local area. Injection may be performed using a syringe 219, as illustrated in FIG. 12A, or other injection tool. After allowing time for the injected anesthesia to take effect, a small incision 223 (e.g., no greater than about ten cm or no greater than about seven cm or no greater than about five cm is made in the skin 125 of the patient 1, with a scalpel 229 or other surgical cutting tool, in a location inferior to the target area where device 10 is to be implanted. In the example shown, the incision 223 is a mid-line para-umbilical incision made substantially below the lower rib line 114. (FIG. 12A shows a frontal schematic view of the abdominal portion of the patient 1).

A delivery tract is then opened from opening 223 through the subcutaneous tissues and abdominal wall to provide an access opening into the abdominal cavity. For example, the delivery tract may be formed by starting with a small incision 223 and then inserting a small port under visual guidance (for example, with VISIPORT™, or the like) to provide safe access into the abdominal cavity. Alternatively, the delivery tract can be made with a cannula and a veress-style needle within it which is subsequently exchanged, after access into the abdominal cavity, with a wire, such as guidewire 502 or a viewing wire to allow exchange of the cannula and insertion of a larger bore access sheath over a dilator over the wire.

Figure 13A:
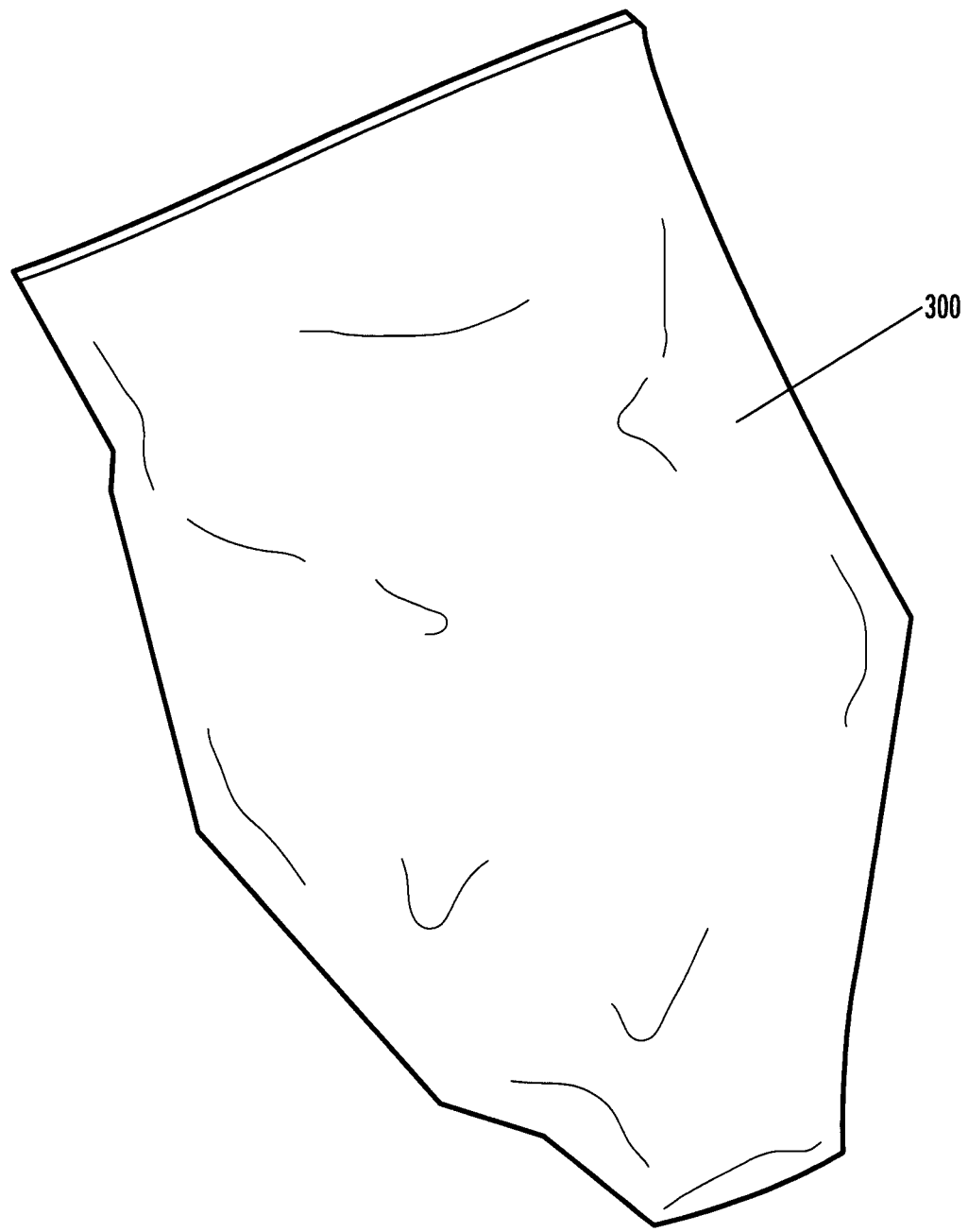
FIG. 13A illustrates an endobag.
Figure 13B:
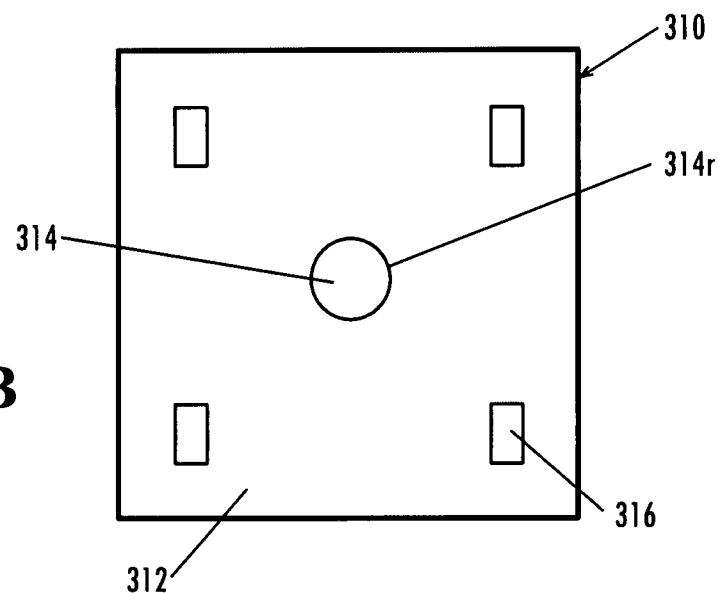
FIG. 13B illustrates a wound protector.

Once the delivery tract has been established, device 10 in a compact configuration is inserted through opening 223 and advanced along the tract, through the opening in the abdominal wall and placed in the abdominal cavity. To protect device 10 from contamination with skin flora, an endobag 300 (see FIG. 13A), such as Endobag #25040 by Covidien, Mansfield, Mass., or the like, may be used to enshroud device 10 to ensure that device 10 does not contact the skin as device 10 is being passed through the opening 223. Additionally, or alternatively, wound protector 310 may be used to ensure that device 10 does not contact the skin of the patient as device 20 is being passed through opening 223. FIG. 13B shows an example of a wound protector that can be used, such as a Steri-Drape™ wound protector (3M Corporation, Minneapolis, Minn.) or the like. Wound protector 310 comprises a sterile plastic sheet 312 with a central opening 314 therein that may optionally be formed by a ring 314r, or opening 314 can be formed in sheet 312 without the ring 314r. Further optionally, sheet 312 may include attachment members 316 about a periphery thereof, such as adhesive strips, or the like. In use, opening 314 (and optionally, ring 314r) are inserted through the opening 223, with the majority of the sheet placed externally of the opening 223 and peripherally thereof to cover the skin of the patient adjacent thereto, in all directions 360 degrees therearound. Device 10 can then be inserted (with or without encapsulation in endobag 300, whereby it is ensured that device 10 does not contact the skin of the patient as it is being inserted through opening 223. Wound protector 310 may also be used in a similar manner when delivery of device 10 is accomplished by other techniques, such as delivery by device 400 (FIG. 16A) or other alternative delivery method.

Once device 10 has been completely delivered through the opening 223 (except for possibly a portion of conduit 12) so there is no risk of the fillable member 10em or attachment tabs 150 contacting the skin 125, endobag 300 can then be removed off of device 10 and removed back out of opening 223. Prior to insertion of device 10 into endobag 300, the device 10 is compacted to give it a smaller cross-sectional size and thus make it easier to pass through opening 223. As noted previously, buoyancy member 10bm is not fillable. Buoyancy member 10bm is also not very compressible, so it is made in a size and shape that facilitates its passage through opening 223. Fillable member 10em is very compressible and, when substantially devoid of fluid, can be wrapped around buoyancy member 10bm so that the device is only slightly larger in cross-sectional area than the cross-sectional of the buoyancy member 10bm alone. This compact form of device 10 is inserted into endobag 300 and endobag 300 may be likewise wrapped around the device. In any event, the surgeon or assistant can maintain the device in this compact configuration by holding it (though the endobag) with a slight, hand compression force. Alternatively, device 10 may be compacted into an alternative delivery tool used to inserted and deploy the device 10, as described in more detail below.

After delivery of device 10 through the abdominal wall and into the abdominal cavity, wherein conduit 12 may be pushed in with the remainder of the device 10, or left extending from the incision wherein, in this case, the incision is closed around the conduit, incision 223 is closed and made airtight to permit insufflation of the abdominal cavity. Trocars/ports 280 are next placed through which a laparoscope can be inserted and tools can be inserted for performing steps of the procedure.

Figure 12B:
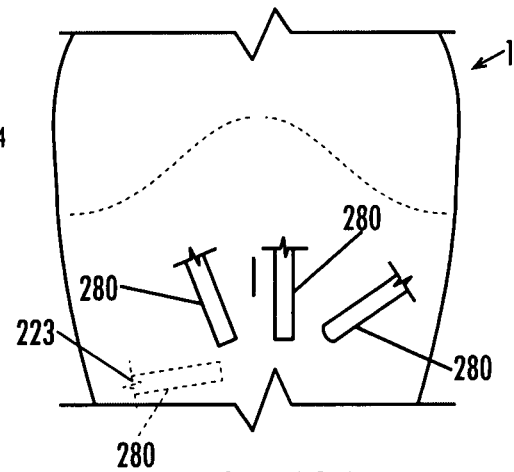
Figure 12C:
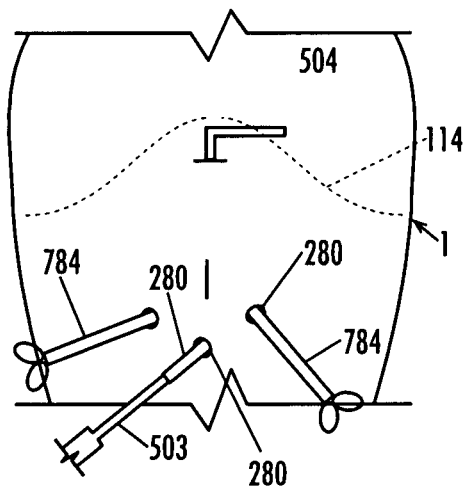
Figure 12D:
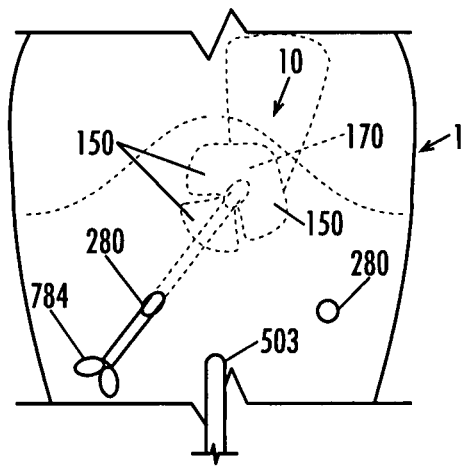

The insufflation can also be performed through one or more of these trocars. For example, standard carbon dioxide insufflation can be performed using a standard trocar e.g., 5 mm trocar, 7 mm trocar, 12 mm trocar, etc. A trocar 280 (e.g., 12 mm trocar) may be placed inferiorly of the closed incision 223, as shown in FIG. 12B for placement of the laparoscope, or alternatively, the trocar 280 may be placed through the incision 223 and the incision can be closed up to the trocar 280 to form a relatively airtight junction that permits insufflation. A 10 mm scope may be inserted through trocar 280. Alternatively a 5 mm scope may be used to allow the use of three 5 mm ports to carry out the procedure. FIG. 12B shows the two additional ports/trocars 280 being arranged for a split-leg procedure, where the additional ports are placed on opposite sides of the port that the endoscope is inserted through. Alternatively, a non-split-leg procedure may be carried out where both of the two additional ports 280 are placed through a single side of the patient 1 (indicated in phantom lines), relative to placement of the port 280 through which the scope is passed. When placing the trocars 280, care should be taken to ensure that the trocars 280 are at least about 10 to about 15 cm away from the locations on the anterior abdominal wall where the inferior borders of the attachment tabs 150 will be located upon fixing the attachment tabs 150 to the interior surface of the abdominal wall.

Alternative to being left extending from the incision, conduit 12 can be extended out of any one of the trocars. Filling of fillable member 10em can be performed just after the initial placement of device 10 into the abdominal cavity. A sterile stopcock can be connected to conduit 12 and a sterile syringe can be used to at least partially fill fillable member 10em with air. The stopcock can then be removed and the tubing can be placed back through the trocar, if extending therefrom, and into the patient 1.

Next, a liver retractor 504 (such as a Nathanson retractor or the like) is inserted through the skin 125, fat 131 abdominal wall 127 and into the abdominal cavity and maneuvered to retract the left lateral segment (part of the left lobe) of the liver 121 superiorly.

Using graspers 784 the device 10 is next maneuvered into a target location where it is to be implanted. Graspers 784 can be used to grasp positioning tab(s) 154 and/or attachment tabs 150 to performing pushing, pulling and/or twisting maneuvers to move and orient device 10 to its desired location. Additionally, graspers 784 or other tools can be used to push on locations of the fillable member 10em that are reinforced by one or more reinforcing layers 160 and/or tabs 150,154. However, portions of fillable member 10em that are not reinforced should neither be grasped nor pushed on, as damage to the wall of the fillable member 10em could result. Placement of the patient 1 in a reverse Trendelenberg position may facilitate maneuvering of the device 10 to its intended location and orientation. The superior portion of the fillable member 10em is placed under the left lateral segment of the liver 121 and the inferior portion of fillable member is placed so that the attachments tabs 150 approach the epigastrium. If device 10 is provided with an attachment tab 154 that includes an Angle of His pointer 154p, then the tab 154 is grasped and pushed so that the pointer 154p aligns with the Angle of His.

At this time, fillable member 10em can be at least partially filled (e.g., partial filling, to the mini volume 10MI, less than the mini volume, or slightly more than the mini volume) with saline or gas so that the surgeon can get a better visualization of the placement and orientation of device 10 by viewing through scope 503. The conduit 12, at this stage can be extended out of any opening in the patient leading into the abdominal cavity. If the surgeon is satisfied with the placement and orientation of device 10, then fillable member 10em can be at least partially deflated to provide more working space and the procedure continues. If the surgeon is not satisfied with the placement or orientation of device 10, then fillable member can be deflated and device 10 is further moved/manipulated in any of the manners described above. Then the partial filling and visual checking procedure can be repeated. These steps can be iterated as many times as necessary until the surgeon is satisfied that device 10 has been properly placed and oriented.

Prior to attaching attachment tabs 150 to the abdominal wall (epigastrium) 127, the falciform ligament is removed and any fat on the interior surface of the abdominal wall is removed from locations that the attachment tabs 150 will overlie when attached. Next a location on the skin 125 is determined that is aligned with a location on the abdominal wall through which loop 170 will be pulled and fixed externally of the abdominal wall. Graspers 784 or other instrument may be used to push up against the abdominal wall at the location overlying loop 170 to help locate this spot externally on the skin 125 of the patient 1. Once the spot on the skin is located, a needle, hooked needle, or other piercing instrument is pushed through the skin at the identified location, through the fat and the abdominal wall. The hooked needle or suture passers 786 or other instrument can then be used to hook, grasp or otherwise attach to the suture 59 that is attached to loop 170. By drawing suture 59 out through the skin 125 of the patient, this draws loop 170 through the abdominal wall. Because only the suture 59 actually extends through the skin 125, this helps to maintain insufflation pressure in the abdominal cavity. Alternatively, a longer loop 170 could be used in place of the short loop 170 and suture 59 shown in FIG. 3A, where the longer loop has sufficient length to be pulled out through the skin 125. However, the porosity and breadth of the loop allow significantly more flow of insufflation gas out through the skin, so the formed technique, using the short loop 170 and suture 59 is preferred.

At this stage, the positioning and orientation of device 10 can again be checked using scope 503 to ensure that the superior end portion of fillable member 10em is located under the left lateral segment of the liver 121 and that no major wrinkles or fold are present in the attachment tabs 150 as they are drawn against the abdominal wall. Thus, the inferior end portion of device 10 is positioned against the anterior abdominal wall (e.g., epigastrium) and the superior end portion extends posteriorly and superiorly into the abdominal cavity as it is positioned behind the left lateral lobe of the liver 121. The free end of conduit 12 can be passed through one of the ports 280 and gas or saline can be inputted therethrough to fill fillable member to at least mini volume 10MI to ensure that no folds or creases exist in the fillable member 10em when filled. After results of checking are satisfactory, fillable member 10em can again be at least partially deflated to provide better working space for continuing procedures.

Next, suturing of the attachment tabs 150 to the abdominal wall is begun. Sutures 180 may be permanent, non-biodegradable sutures, or they may be bioresorbable such that they provide mechanical attachment of the attachment tabs to the abdominal wall, holding the ingrowth patches 152 in approximation (contact) with the abdominal wall to allow tissue ingrowth into them, such that attachment tabs 150 become ingrown with tissue and thus securely fixed to the abdominal wall. When bioresorbable, sutures 180 are designed to resorb over time, but not before adequate tissue ingrowth into ingrowth patches 152 has occurred.

In either case, sutures 180 are folded back and forth upon themselves in pairs (in a manner similar to folding an electrical cord) and the folded sutures are retained in loops 182 fixed in tabs 150 (see FIG. 3A). The free ends of the sutures are left slight extending so that they can be readily grasped (such as by graspers 784) and pulled free from loop 182, whereupon the sutures 180 unfold, ready for use. Sutures 180 and/or loops 182 can also be alternately color-coded to assist the surgeon in keeping track of the order in which the sutures are selected and passed through the abdominal wall and skin.

To create a working space, loop 170 is grasped in the abdominal cavity and pulled back through the abdominal wall somewhat to establish a space between attachment tabs 150 and the abdominal wall. Tension is maintained on suture 59 outside of the skin to also maintain tension on loop 170 so as to maintain tabs 150 at a desired distance from the abdominal wall. Suturing of the attachment tabs 150 is typically begun with the cephalad-most positioned sutures 180 with the surgeon working down around both sides to the inferiorly placed sutures 180.

Figure 14A:
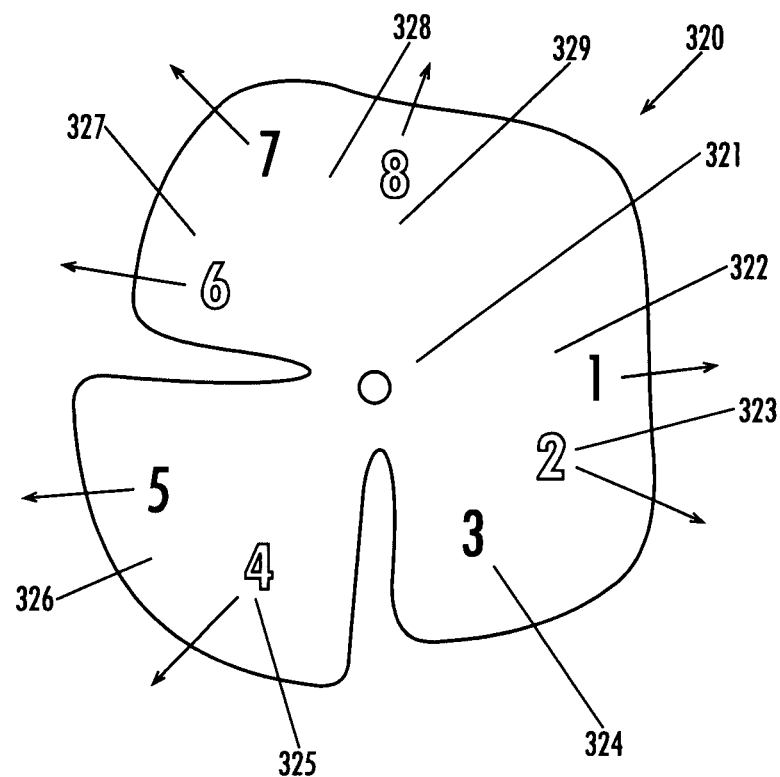
FIG. 14A illustrates a suture template according to the present invention.
Figure 14B:
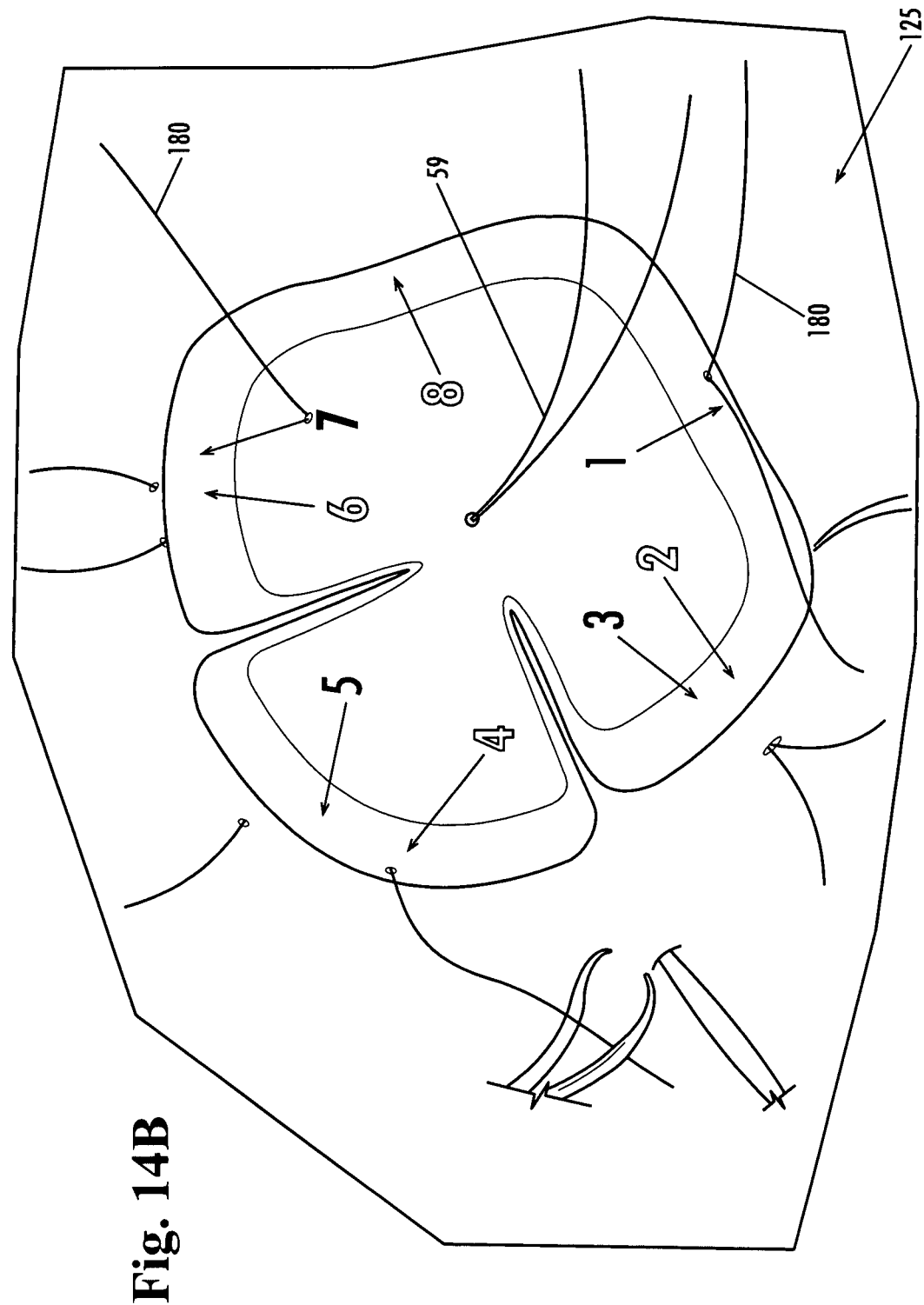
FIG. 14B illustrates a suture template having been applied to the skin of a patient.

A suture placement template 320 (see FIG. 14A) may be placed over the skin of the patient, with suture 59 passing through a center marking or opening 321 thereof and oriented to align with the positions of the sutures 180 on the attachment tabs 152 underlying the abdominal wall. Template 320 may include markings and/or openings 322-329 that indicate the approximate locations on the skin through which the sutures will be passed and optionally, the order in which each suture will be passed. Markings 322-329 may also be alternately color-coded, or otherwise differentiated to assist in keeping track of the order in which the sutures are passed. According to one technique, once a first suture has been passed through the skin 125 in a proper location, it can be passed through the template 320. At this point, since suture 59 is also passed through the center of the template 320 this is enough to orient the template fairly accurately to locate the approximately correct locations to pass a suture passer 786 for pulling the remainder of sutures 180 through correctly aligned locations. FIG. 14B shows a clear silicone template having been properly oriented with the underlying sutures 180 and placed on the skin of a patient. Alternatively, two or more of the indicators 322-329 may be made radiopaque, and two or more loops 182 that correspond in position to the two or more indictors 322-329 (or at least any two predetermined locations on template 320 and corresponding locations on attachment tabs 150) may be made radiopaque. In this manner, template 320 can be properly aligned with the underlying attachment tabs 150 by alignment of the radiopaque markings on template 320 with the corresponding radiopaque markings on attachment tabs 150, so that the surgeon or assistant will be reasonably well informed as to even the location on the skin to pass the suture passer 786 through to engage even the first suture 180 to be pulled through the skin 125.

Sutures 180 are passed through the appropriate locations in the skin by grasping a suture pair with graspers 784 and pulling them out of loop 182, and then passing one suture 180 at a time to suture passers 786 having been passed through the skin at the appropriate location, through the abdominal wall, and into the abdominal cavity. Care is taken to ensure that the sutures do not become entangled or twisted with other sutures as they are passed through the abdominal wall 127, fat 131 and skin 125.

Figure 12E:
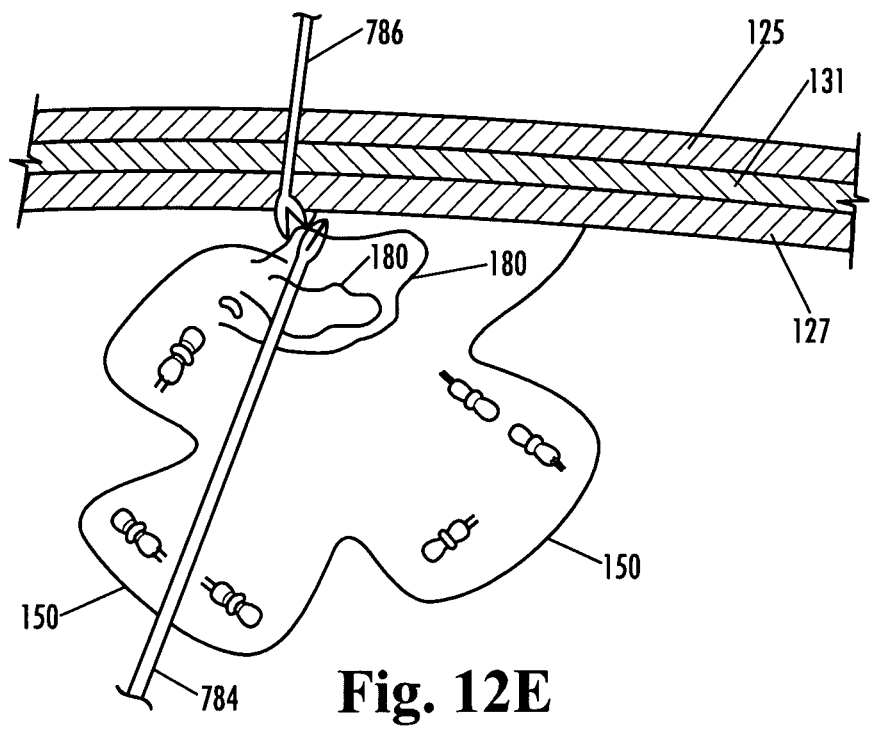
Figure 12F:
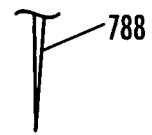

Whether or not template 320 is used, a finder needle 788 (see FIG. 12F) may be used to first pass through a location of the skin 125, fat 131 and abdominal wall 127 thought to be a correct location for passing a suture. Scope 503 can then be used to visualize the location of the finder needle in the abdominal cavity to determine whether it lines up satisfactorily with the location of the suture 180 that is to be pulled therethrough. If the alignment is not close enough, the finder needle 788 can be withdrawn and reinserted at another location. This process of insertion and visualization to determine alignment can be repeated until a satisfactory location has been found. Once a satisfactory location has been found, the finder needle is removed out of the skin 125, and a small nick is made in the skin 125 (e.g., about 3 mm in length or less, using a scalpel or the like) and then suture passers 786 are passed through the skin at the location of the nick. Suture passers 786 may be Close-Sure suture passers from Inlet Medical, suture passers produced by Gore, Inc., or other suture passer tools that are commonly available. FIG. 12E illustrates the surgeon having grasped a suture 180 to be passed with graspers 784 (inserted through one of ports 280) and suture passers 786 having been passed through the skin 125, fat 131 and abdominal wall 127. Suture 180 is passed, using the graspers 784 into the jaws of the suture passer 786. The jaws of the suture passer 786 are then closed and the suture is released by the graspers 784. The suture passer 786 is then drawn back through the abdominal wall 127, fat 131 and out of the skin 125 so that the free end of suture 180 extends out of the skin 125.

This process is repeated until all sutures 180 have been drawn out of the skin at the appropriate locations overlying the locations where the sutures 180 attach to the attachment tabs 150. Once all of the sutures 180 have been passed, sutures 180 and loop 170 (via suture 59) are drawn up through the abdominal wall to draw the attachment tabs 150 against the abdominal wall. Inspection is then performed via scope 503 to determine whether the tabs 150 are being properly positioned. Proper positioning includes a lack of folds in the attachment tabs that would prevent substantial portions of the ingrowth patches from contacting the abdominal wall. Existence of such folds could impair the amount of ingrowth attachment provided, and this is unsatisfactory. If one or more sutures 180 need to be passed through different locations to remove folds or other inappropriate placement of the tabs 150, this is done, using the same techniques described above. In any case, once it has been confirmed that the attachment tabs 150 are properly placed, insufflation pressure can be dropped from the working pressure of about 15 mm Hg to about 5 mm Hg, and sutures 180 of the suture pairs are tied together and pushed against the fascia/external surface of the abdominal wall, to securely anchor tabs 150 against the internal surface of the abdominal wall. Likewise, loop 170 is sutured to the fascia/external surface of the abdominal wall using suture 59.

Figure 12G:
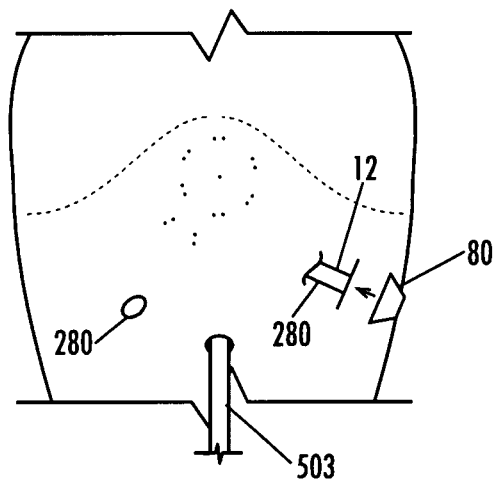

An access member 80 is next connected to the free end of conduit 12 (after cutting the conduit 12 to an appropriate length that extends only about to the location where the access member 80 is to be implanted. FIG. 12G illustrates installation of access member 80 onto the free end of conduit 12. Fillable member 10em may optionally be at least partially filled with saline prior to installing access member 80.

Access member 80 can be installed subcutaneously with sutures, hooks or stables as know for subcutaneous access ports/members.

Once access member 80 has been anchored, and any tools remaining in the abdominal cavity (if any) have been removed, if fillable member 10em is not already filled to mini volume 10MI with saline, a filling tool, such as a syringe (e.g., 60 cc syringe) or other specifically defined filling tool is engaged with access member 80 and fillable member 10em is filled with saline to the mini volume 10MI. Any remaining openings through the skin of the patient are closed to complete the procedure. Optionally, fillable member 10em may be filled to the target volume 10T or more or less to begin effective treatment immediately. Alternatively, fillable member 10em may be left at the mini volume 10MI for a time to allow tissue ingrowth into attachment tabs 150 and general healing of the patient. On a follow-up visit, the physician can then fill the fillable member up to a working volume around the target volume 10T or more or less.

Filling the fillable member to the mini volume 10MI or more may take multiple injections, particularly when a 60 cc syringe is used. Further, because of the additional constriction introduced by the valve mechanism of the access member and smaller diameter passageways, compared to inputting saline directly into conduit 12, driving the plunger of the syringe can be quite onerous on the hand of the user, with substantial pressure of the syringe handle occurring against the user's hand as the saline is driven through the access member 80, conduit 12 and into fillable member 10em.

Figure 15A:
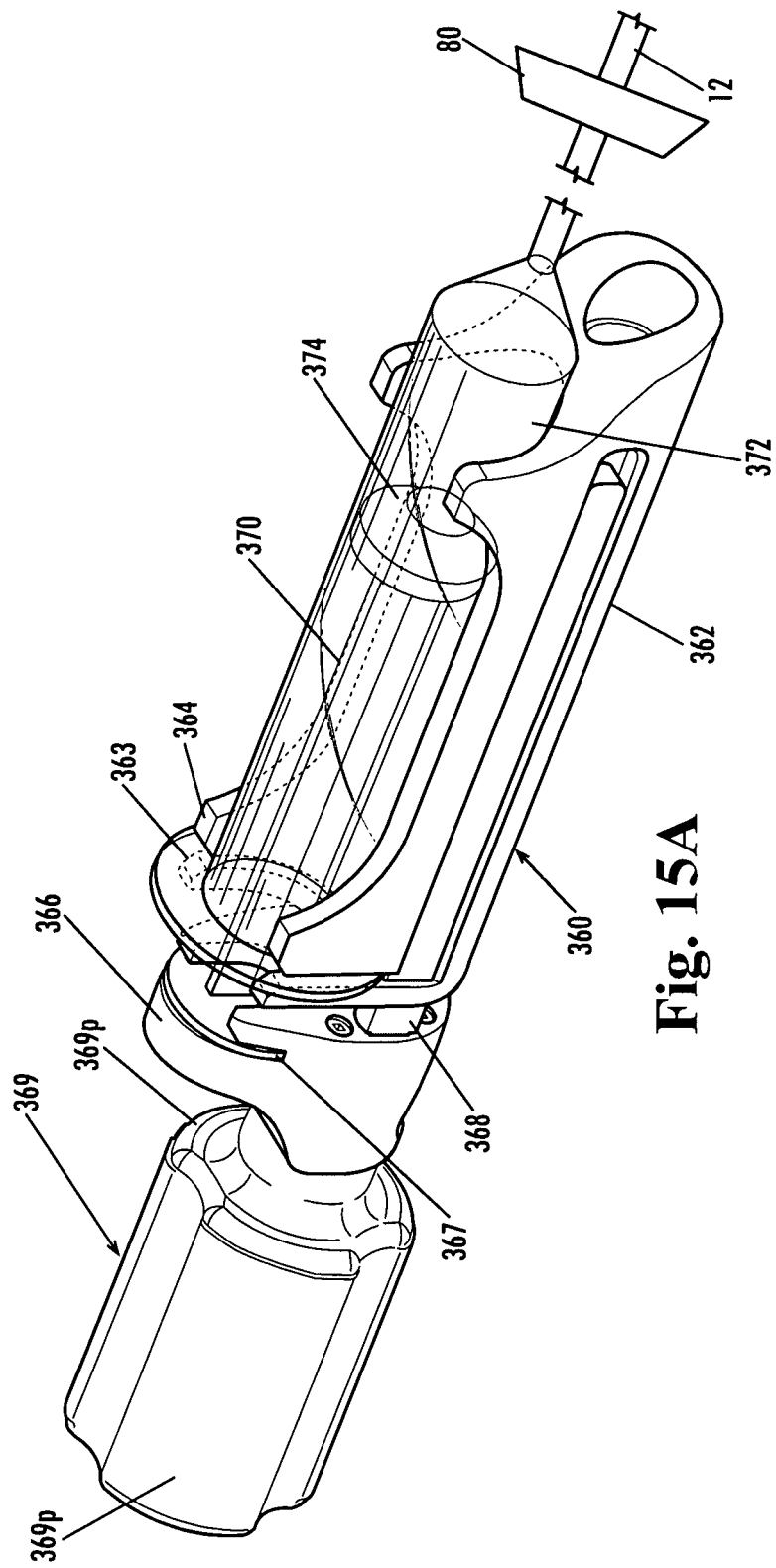
FIG. 15A illustrates an adjustment aid tool that does not require a pushing pressure against the hand of the user to deliver saline out of a syringe.
Figure 15B:
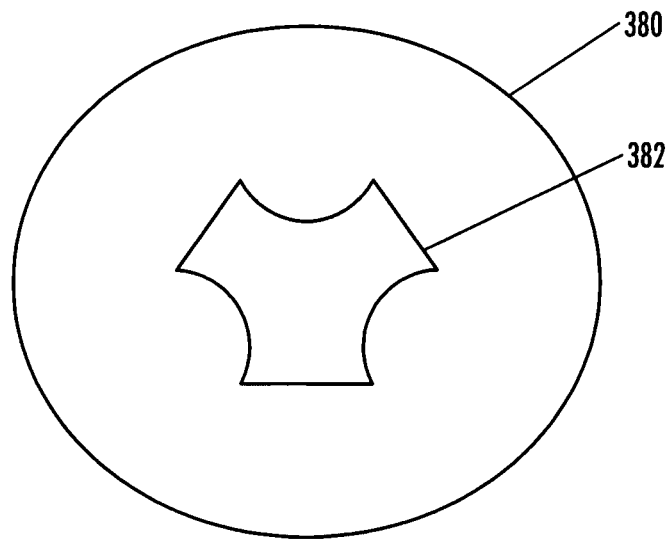
FIG. 15B shows a proximal end view of a ring that can be used with the tool of FIG. 15A.

Accordingly an adjustment aid tool 360 is provided that does not require a pushing pressure against the hand of the user to deliver saline out of a syringe, see FIG. 15A. Tool 360 has a main frame portion 362 configured to receive the barrel 372 of a syringe 370 therein, and having stops 364 that abut against the flanges at the proximal end of the barrel 372 to prevent forward movement of the barrel 372 when plunger 374 is advanced into the barrel 372. A drive carriage 366 is threaded over a drive screw 368 and is advanced or retracted relative to main frame portion 362 depending upon the direction of rotation of handle 369 by the user, handle 369 being fixed to drive screw 368. Carriage 366 includes slot 367 configured to receive the distal end shoulder of the plunger driver 376. Distal stops 363 may also be present to prevent barrel 372 from moving proximally when plunger 374 is drawn back out of the barrel 372. In one particular embodiment, drive screw 363 has a pitch that provides two inches of advancement of plunger 374 per rotation of handle 369. Accordingly, saline can be rapidly expressed from syringe 370 and inputted to fillable member 10em using tool 360, with much less pain to the user, particularly when multiple syringe volumes are being delivered.

Figure 15C:
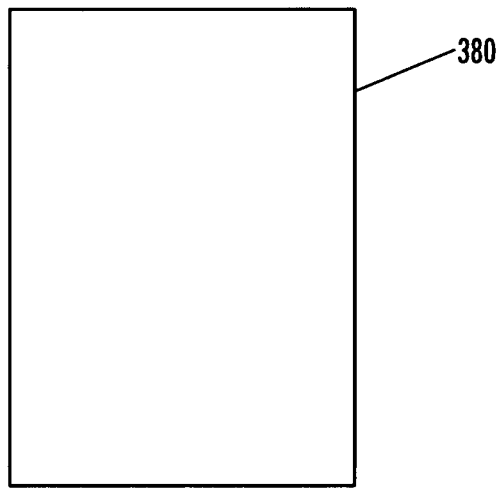
FIG. 15C shows a side view of the ring of FIG. 15B.

Optionally, a ring 380 may be provided that is configured to slide over handle 369 and provide even greater mechanical advantage to the user, so that the ringed handle is easier to turn to expel saline from syringe 370. For example, ring 380 may have a diameter that is greater than the diameter of handle 369 by about one to about three inches In one embodiment, handle 369 has an outside diameter or about two inches and ring 380 has an outside diameter of about three inches. In another embodiment, handle 369 has an outside diameter or about two inches and ring 380 has an outside diameter of about four inches. Alternative to ring 380, a lever can be made that is mountable to handle 369 and which extends in a radial direction therefrom to provide added mechanical advantage to turn the handle 369. Ring 380 has recesses 382 that match protrusions 369p on handle 369 so that ring 380 slides over handle 369 and receives protrusions 369p in recesses 382, thereby preventing rotation of handle 380 with respect to handle 369. The length of the ring 380 (see side view of FIG. 15C) may vary depending upon what is comfortable to the user and/or weight considerations. The tool 360 shown in FIG. 15A is specifically designed for use with a 60 cc syringe. However, tool 360 may be downsized or upsized accordingly to be used with syringes of different capacities.

Figure 16A:
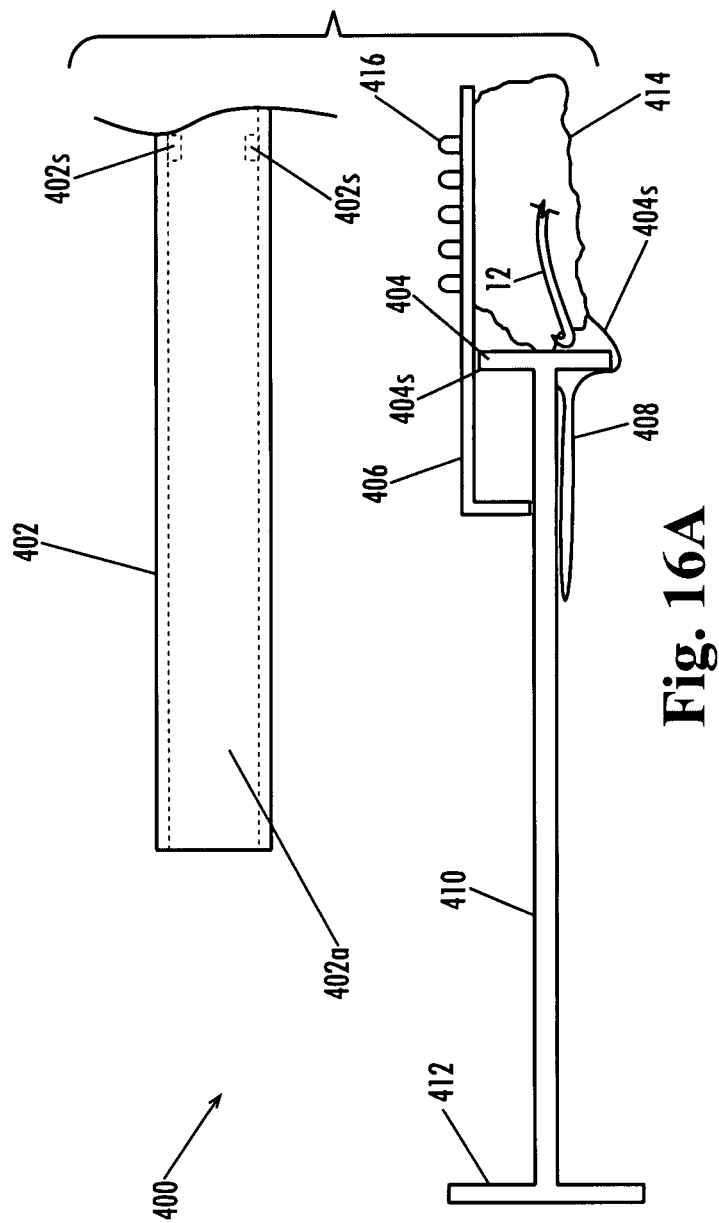
FIG. 16A illustrates components of a delivery tool that may be used as an alternative to the endobag shown in FIG. 13A.

FIG. 16A illustrates components of a delivery tool 400 that may be used as an alternative to the endobag 300 described above. Tool 400 includes a delivery tube 402 dimensioned to received device 10 in a compact configuration so that device 10 can be delivered through tube 402 past the incision 223, across the abdominal wall and into the abdominal cavity. Accordingly tube 402 has an outside diameter that permits it to be inserted through incision 223 and the tract leading into the abdominal cavity. In one embodiment, tube 402 has an outside diameter of about two inches. The diameter of tube 402 may vary according to the size of the device 10 to be implanted and the extent to which it can be compressed for delivery through tube 402. Tube 402 may have a length of about eight inches to about ten inches, but this can also vary depending upon the size and compressed length of the device 10 being delivered through tube 402.

A plunger 404 is configured to be received in the annulus of tube 402 with sufficient tolerance to allow mandrel 406 and tether 408 to also be received in the annulus. Alternatively, plunger 404 may have a tighter tolerance with the annulus, but be provided with slots 404s into which mandrel 406 and tether 408 are received. A rigid plunger shaft 410 having a length sufficient to extend handle 412 (attached to the proximal end of shaft 410) out of the proximal end of tube 402 when plunger 404 is flush or nearly flush with the distal end of tube 402. Tube 402 may be provided with one or more shoulders or stops 402s at a distal end of the annulus 402a to prevent plunger 404 from being pushed out of the distal end of tube 402. The inner wall of tube 402 defining the annulus 402a may be coated with a lubricious coating, such as polytetrafluoroethylene, or the like.

Figure 16B:
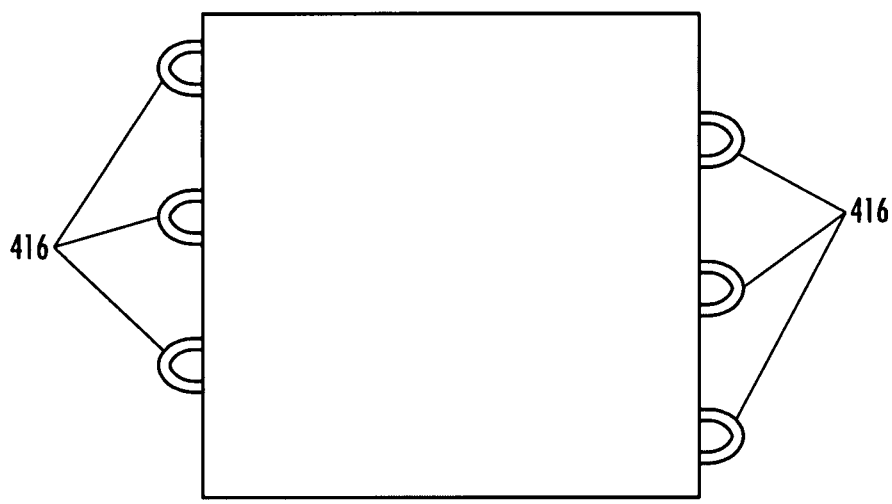
FIG. 16B illustrates a sheath that can be used as a component of, or in conjunction with the tool shown in FIG. 16A.

A sheath 414 is provided to wrap around device 10 when in a compact configuration (see FIG. 16B), and to maintain device 10 in the compact configuration until released. For example, sheath 414 may be made from a sheet of lubricious material, such as polytetrafluoroethylene or the like. As noted previously, device 10 can be compacted by wrapping the deflated fillable member 10em around buoyancy member 10bm. Sheet 414 is provided with sets of loops 416 on opposite sides thereof, with the loops 416 on one side being offset from the loops on the opposite side, as shown in FIG. 16B. Accordingly, device 10 in the compact configuration can be placed on sheet 414 between the sets of loops 416 and then the sides of sheet 414 can be rolled around the compacted device to align the offset loops 416. Once aligned, mandrel 406, which may be resiliently flexible, is skewered through the aligned loops 416, thereby locking sheet 414 around device 10 and maintaining device 10 in a compact configuration, as illustrated in FIG. 16A.

Device 10 sheet 414 and plunger 404 are next inserted into delivery tube 402 and the device 10/sheet 414 can be advanced up into the distal end portion of tube 402. Device 10 and sheet 414 can then be advanced through incision 223 and the tract leading into the abdominal cavity until the distal end portion of tube 402 has entered the abdominal cavity. Next device 10/sheet 414 are expelled from tube 402 by pushing forward on handle 412 while holding tube 402 stationary, thereby advancing plunger 404 until device 10/sheet 414 have been completely expelled from the tube 402. Next, handle 412 is pulled back on while holding tube 402 stationary thereby withdrawing mandrel 406 (which is fixed relative to plunger shaft 410 out of loops 416. This releases sheet 414 from its compressive hold on device 10 thereby deploying device 10. Next, the tool 400 can be removed from the delivery tract and incision 223 (i.e., from the patient) as a unit. Sheet 414 is tethered to plunger shaft 410/plunger 404 by a tether 408 that is longer than the length of the portion of mandrel 406 that extends distally of plunger 404. Accordingly, tether 408 does not draw against sheet 414 when the plunger is initially partially withdrawn to remove mandrel 406 form loops 416. However, as tool 400 is withdrawn as a unit, tether 408 draws sheet 414 along with it, out of the patient 1.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating a patient, said method comprising:
   measuring at least one measurement of anatomy in an abdominal space internal to the rib cage of the patient with a measuring device; and
   selecting an appropriately sized device, wherein the device comprises a single expandable member having different length and diameter dimensions and an attachment member attached thereon, said attachment member configured to be attached to an internal abdominal structure in the abdominal cavity and maintain the expandable member in abutment to the internal abdominal structure, said attachment member having a free end extending from the expandable member, for implantation into the abdominal cavity of the patient, based on the at least one internal measurement taken;
   wherein said measuring at least one internal measurement includes measuring both Lateral and AP measurements.

2. The method of claim 1, wherein said AP measurement is taken by measuring a distance from a posterior inside surface of a rib of the patient at a level of and through the center of the gastroesophageal junction to an anterior inside surface of the rib at the level of the gastroesophageal junction; and the Lateral measurement is taken from midline to a left lateral inside surface of the rib, through the center of the location of the gastroesophageal junction, at the level of the gastroesophageal junction.

3. A method of treating a patient, said method comprising:
   measuring at least one measurement in an abdominal space internal to the rib cage of the patient with a measuring device; and
   selecting a single appropriately sized device for implantation into the abdominal cavity of the patient, based on the at least one internal measurement;
   wherein said measuring at least one internal measurement includes measuring at least a Lateral measurement and an AP measurement.

* * * * *